United States Patent
Tang et al.

(10) Patent No.: US 11,712,215 B2
(45) Date of Patent: Aug. 1, 2023

(54) DEVICES, SYSTEMS, AND METHODS FOR MOTION-CORRECTED MEDICAL IMAGING

(71) Applicant: CANON MEDICAL SYSTEMS CORPORATION, Tochigi (JP)

(72) Inventors: Qiulin Tang, Buffalo Grove, IL (US); Liang Cai, Vernon Hills, IL (US); Zhou Yu, Glenview, IL (US); Jian Zhou, Buffalo Grove, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 179 days.

(21) Appl. No.: 17/229,247

(22) Filed: Apr. 13, 2021

(65) Prior Publication Data

US 2022/0323035 A1 Oct. 13, 2022

(51) Int. Cl.
*A61B 6/00* (2006.01)
*A61B 6/03* (2006.01)
*G06T 11/00* (2006.01)
*G06T 7/11* (2017.01)

(52) U.S. Cl.
CPC ............ *A61B 6/5264* (2013.01); *A61B 6/032* (2013.01); *A61B 6/5205* (2013.01); *G06T 7/11* (2017.01); *G06T 11/005* (2013.01); *G06T 11/006* (2013.01); *G06T 2211/436* (2013.01)

(58) Field of Classification Search
CPC ..... A61B 6/032; A61B 6/5205; A61B 6/5264; G06T 7/11; G06T 11/005; G06T 11/006; G06T 11/2211; G06T 11/436
See application file for complete search history.

(56) References Cited

U.S. PATENT DOCUMENTS

| | | | |
|---|---|---|---|
| 8,600,132 B2 | 12/2013 | Razifar | |
| 9,189,851 B2 | 11/2015 | Liao | |
| 9,576,357 B2 | 2/2017 | Averikou | |
| 9,799,100 B2 | 10/2017 | Guo | |
| 2007/0183639 A1 | 8/2007 | Kohler | |
| 2011/0142315 A1 | 6/2011 | Hsieh | |
| 2012/0275656 A1 | 11/2012 | Boese | |
| 2014/0334702 A1 | 11/2014 | El Fakhri | |

(Continued)

OTHER PUBLICATIONS

Joscha Maier et al., Coronary Artery Motion Compensation for Short-Scan Cardiac CT Using a Spatial Transformer Network, The 6th International Conference on Image Formation in X-Ray Computed Tomography, Aug. 6, 2020.

(Continued)

*Primary Examiner* — Mark R Gaworecki
(74) *Attorney, Agent, or Firm* — Canon U.S.A., Inc. IP Division

(57) ABSTRACT

Devices, systems, and methods receive scan data that were generated by scanning a region of a subject with a computed tomography apparatus; generate multiple partial angle reconstruction (PAR) images based on the scan data; obtain corresponding characteristics of the multiple PAR images; perform correspondence mapping on the multiple PAR images based on the obtained corresponding characteristics and on the multiple PAR images, wherein the correspondence mapping generates correspondence-mapping data; and generate a motion-corrected reconstruction image based on the correspondence-mapping data and on one or both of the scan data and the PAR images.

22 Claims, 23 Drawing Sheets

(56) References Cited

U.S. PATENT DOCUMENTS

| | | | |
|---|---|---|---|
| 2018/0005414 A1* | 1/2018 | Lee | G06T 11/003 |
| 2018/0040145 A1 | 2/2018 | Matthews | |
| 2018/0204330 A1 | 7/2018 | Ra | |
| 2018/0268574 A1 | 9/2018 | Lilja | |
| 2019/0108904 A1 | 4/2019 | Zhou | |
| 2019/0353741 A1 | 11/2019 | Bolster, Jr. | |
| 2020/0118308 A1 | 4/2020 | Nakanishi | |
| 2020/0118669 A1 | 4/2020 | Mohr | |

OTHER PUBLICATIONS

Qiulin Tang et al., A fully four-dimensional, iterative motion estimation and compensation method for cardiac CT, Jun. 25, 2012.

A. Sisniega et al., Local Motion Estimation for Improved Cone-Beam CT Deformable Motion Compensation, The 6th International Conference on Image Formation in X-Ray Computed Tomography, Aug. 6, 2020.

Guotao Quan et al., Cardiac Motion Correction of Computed Tomography (CT) with Spatial Transformer Network, The 6th International Conference on Image Formation in X-Ray Computed Tomography, Aug. 6, 2020.

Alexander Katsevich et al., A Motion Estimation and Compensation Algorithm for 4D CBCT with Cyclic Deformation Model, The 6th International Conference on Image Formation in X-Ray Computed Tomography, Aug. 6, 2020.

Markus Susenburger et al., 4D Segmentation-Based Anatomy-Constrained Motion-Compensated Reconstruction of On-Board 4D CBCT Scans, The 6th International Conference on Image Formation in X-Ray Computed Tomography, Aug. 6, 2020.

Matt D. Holbrook et al., Deep Learning Based Distortion Correction and Material Decomposition for Photon Counting CT: A Simulation Study, The 6th International Conference on Image Formation in X-Ray Computed Tomography, Aug. 6, 2020.

Igor Peterlik et al., Motion Resilient Iterative 3D CBCT Reconstruction Based on Gradient Weighting, The 6th International Conference on Image Formation in X-Ray Computed Tomography, Aug. 6, 2020.

T. Lossau et al., Motion Estimation and Correction in Cardiac CT Angiography Images using Convolutional Neural Networks, Jun. 2019.

Karantzalos, et al., "Higher Order Polynomials, Free Form Deformations and Optical Flow Estimation", IEEE International Conference on Image Processing, Sep. 2005.

* cited by examiner

DEVICES, SYSTEMS, AND METHODS FOR MOTION-CORRECTED MEDICAL IMAGING

BACKGROUND

Technical Field

This application generally concerns medical imaging.

Background

Medical imaging can produce images of the internal members of a patient's body. For example, computed tomography (CT) scans use multiple x-ray images of an object, which were taken from different angles, to generate an image of the interior of the object. Other medical-imaging modalities include, for example, X-ray radiography, ultrasonography, magnetic-resonance imaging (MRI), and positron emission tomography (PET). Once the images have been produced, a physician can use the images to diagnose a patient's injuries or diseases.

SUMMARY

Some embodiments of a medical image processing apparatus comprise receiving circuitry configured to receive scan data that were generated by scanning a region of a subject with a computed tomography apparatus; and processing circuitry configured to perform the following: generating multiple partial angle reconstruction (PAR) images based on the scan data, obtaining corresponding characteristics of the multiple PAR images, correspondence mapping on the multiple PAR images based on the obtained corresponding characteristics and on the multiple PAR images, wherein the correspondence mapping generates correspondence-mapping data, and generating a motion-corrected reconstruction image based on the correspondence-mapping data and on one or both of the scan data and the PAR images.

Some embodiments of a medical image processing apparatus comprise receiving circuitry configured to receive scan data, wherein the scan data include multiple sets of scan data; and processing circuitry configured to perform the following: generating partial angle reconstruction (PAR) images based on the scan data, transforming at least one of the PAR images based on characteristics of the multiple sets of scan data to obtain one or more transformed PARs, generating a motion map based on image registration that is performed at least on the transformed PARs, and generating an inverse transform of the motion map, thereby generating a transformed motion map.

Some embodiments of a medical image processing system comprise one or more medical image processing apparatuses for correcting motion artifacts in a medical image, wherein each of the one or more medical image processing apparatuses includes one or more respective computer-readable media and one or more respective processors, and wherein the one or more respective computer-readable media and one or more respective processors of the one or more medical image processing apparatuses cooperate to perform operations that include the following: receiving scan data that were generated by scanning a region of a subject with a computed tomography apparatus; generating multiple partial angle reconstruction (PAR) images based on the scan data; obtaining corresponding characteristics of the multiple PAR images; performing correspondence mapping on the multiple PAR images based on the obtained corresponding characteristics and on the multiple PAR images, wherein the correspondence mapping generates correspondence-mapping data; and generating a motion-corrected reconstruction image based on the correspondence-mapping data and on one or both of the scan data and the PAR images.

Some embodiments of a method comprise receiving scan data that were generated by scanning a region of a subject with a computed tomography apparatus; generating multiple partial angle reconstruction (PAR) images based on the scan data; obtaining corresponding characteristics of the multiple PAR images; performing correspondence mapping on the multiple PAR images based on the obtained corresponding characteristics and on the multiple PAR images, wherein the correspondence mapping generates correspondence-mapping data; and generating a motion-corrected reconstruction image based on the correspondence-mapping data and on one or both of the scan data and the PAR images.

Some embodiments of one or more computer-readable storage media store instructions that, when executed by one or more computing devices, cause the one or more computing devices to perform operations that comprise receiving scan data that were generated by scanning a region of a subject with a computed tomography apparatus; generating multiple partial angle reconstruction (PAR) images based on the scan data; obtaining corresponding characteristics of the multiple PAR images; performing correspondence mapping on the multiple PAR images based on the obtained corresponding characteristics and on the multiple PAR images, wherein the correspondence mapping generates correspondence-mapping data; and generating a motion-corrected reconstruction image based on the correspondence-mapping data and on one or both of the scan data and the PAR images.

Some embodiments of a method comprise receiving scan data, wherein the scan data include multiple sets of scan data; generating partial angle reconstruction (PAR) images based on the scan data; transforming at least one of the PAR images based on characteristics of the multiple sets of scan data to obtain at least one transformed PAR image; generating a motion map based on image registration that is performed on the at least one transformed PAR image; and generating an inverse transform of the motion map, thereby generating a transformed motion map.

DESCRIPTION

Figure 1A:
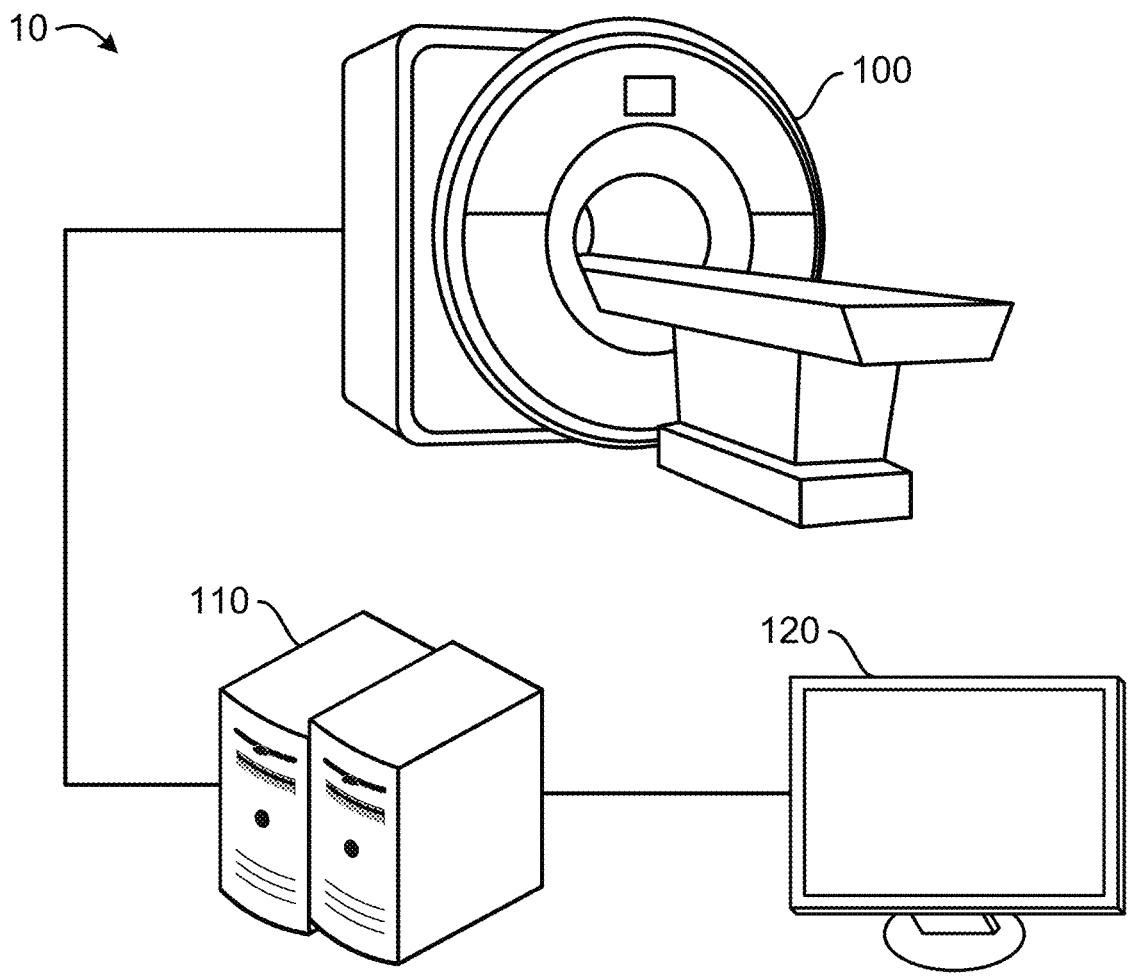
FIG. 1A illustrates an example embodiment of a medical-imaging system.

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein. Furthermore, some embodiments include features from two or more of the following explanatory embodiments.

Also, as used herein, the conjunction "or" generally refers to an inclusive "or," although "or" may refer to an exclusive "or" if expressly indicated or if the context indicates that the "or" must be an exclusive "or."

Additionally, in this description and the drawings, an alphabetic suffix on a reference number may be used to indicate one or more specific instances of the feature identified by the reference numeral. For example, partial angle reconstructions (PARs) may be identified with the reference numeral 1021 when a particular partial angle reconstruction (PAR) is not being distinguished. However, 1021A may be used to identify one or more specific PARs or when the one or more specific PARs are being distinguished from other PARs.

FIG. 1A illustrates an example embodiment of a medical-imaging system 10. The medical-imaging system 10 includes at least one scanning device 100; one or more image-generation devices 110, each of which is a specially-configured computing device (e.g., a specially-configured desktop computer, a specially-configured laptop computer, a specially-configured server); and a display device 120.

The scanning device 100 is configured to acquire scan data by scanning a region (e.g., area, volume, slice) of a subject (e.g., a patient), and the region of the subject may include one or more objects (e.g., organs, vessels). The scanning modality may be, for example, computed tomography (CT), positron emission tomography (PET), X-ray radiography, magnetic resonance imaging (MRI), and ultrasonography.

The one or more image-generation devices 110 obtain scan data from the scanning device 100 and generate a reconstruction of the scanned region based on the scan data. Also, the reconstruction includes one or more reconstructed images of the scanned region. To generate the reconstruction, for example when the scan data include groups of scan data that were acquired at different angles or positions, the one or more image-generation devices 110 perform a reconstruction process on the scan data. Examples of reconstruction processes include filtered back projection (e.g., Radon transform) and iterative reconstruction.

After the one or more image-generation devices 110 generate the reconstruction of the scanned region, the one or more image-generation devices 110 send the reconstruction to the display device 120, which displays one or more reconstructed images from the reconstruction.

When scanning a scanned region (e.g., a scanned region of a subject), some of the components of the scanning device 100 may move. For example, a radiation emitter and a radiation detector that are positioned on opposite sides of a subject may move while scanning the subject. The generated scan data include sets (e.g., groups) of scan data, each of which was acquired at a respective angle. However, an object (e.g., a part of a subject) may move while the radiation emitter and the radiation detector are moving and scanning the object, which may cause the groups of scan data to acquire scan data of the object while the object is in different positions. For example, if the scanning device 100 is a CT scanner and if the object is a beating heart or a cardiac vessel (e.g., a coronary artery), the heart or cardiac vessel may move while the CT scanner acquires scan data from multiple angles. Accordingly, a reconstructed image of the object may be blurred. The one or more image-generation devices 110 are configured to perform motion-correction operations while generating reconstructed images. The same problem can occur when the object to be imaged is a lung, tracheas, or bronchi.

Also, some embodiments of the one or more image-generation devices 110 allow motion correction to be enabled and disabled. For example, some embodiments of the scanning device 100 use cardiac signal monitoring (e.g., electrocardiography) when scanning, which may reduce motion blur in the scanned region. Also for example, some embodiments of the scanning device 100 use cardiac signal monitoring when scanning a heart in order to capture groups of scanned data when the heart is at or close to its quiet phase. However, this may cause the scanning process to consume more time (operate more slowly). Also, if the heart rate changes during scanning, timing the acquisition of the scanned data so that the heart is in the same position each time that scan data is acquired could be difficult. Consequently, scanned data that are acquired using cardiac signal monitoring may still include motion blur (even if the motion blur is reduced). Thus, because motion correction may or may not be desired in various circumstances, some embodiments of the one or more image-generation devices 110 allow motion correction to be enabled and disabled.

Figure 1B:
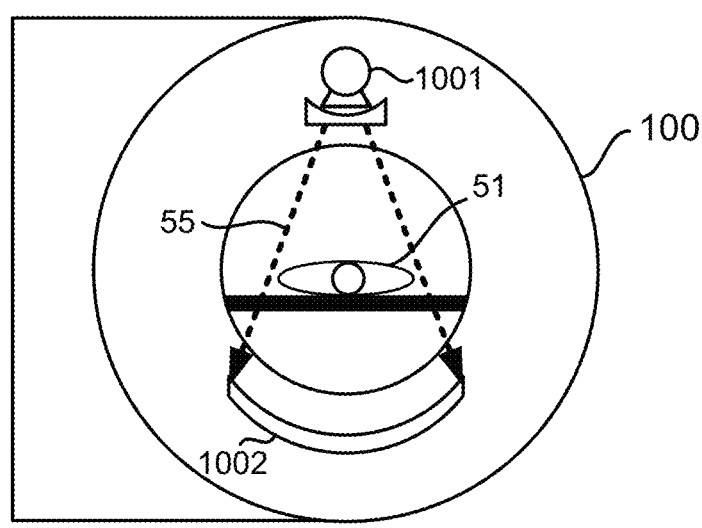
FIG. 1B illustrates an example embodiment of a scanning device.

FIG. 1B illustrates an example embodiment of a scanning device 100. The scanning device 100 includes a radiation emitter 1001 and a radiation detector 1002, which are positioned on opposite sides of a subject 51. The radiation emitter 1001 emits radiation 55 (e.g., x-rays) that travels through a scanned region of the subject 51 and is detected by the radiation detector 1002. The radiation detector 1002 generates scan data (e.g., groups of scan data 1011) based on the detected radiation 55. In this embodiment, the radiation emitter 1001 emits the radiation in the form of a tapering beam (e.g., a rectangular pyramid, a square pyramid, a circular cone, an elliptical cone). Additionally, the radiation detector 1002 has a curved detection surface. But, in some embodiments, the radiation emitter 1001 emits the radiation in the form of parallel beams, or the radiation detector 1002 has a flat detection surface.

Also, the radiation emitter 1001 and the radiation detector 1002 are configured to rotate around the subject 51. Thus, at different angles relative to the subject 51, the radiation emitter 1001 emits radiation 55 that travels through the scanned region of the subject 51 and is detected by the radiation detector 1002. And, at each of the angles, the radiation detector 1002 generates a respective group of scan data 1011. The angles collectively define an angular scanning range. For example, in some embodiments, the angular scanning range is 0 to 180°, and in some embodiments the angular scanning range is 0 to 360°. Additionally, some embodiments of the scanning device 100 generate respective groups of scan data at 900 to 1,200 angles. Thus, for example, if the scanning device generates groups of scan data at 900 angles that range from 0 to 180° and that are evenly spaced, then the increment between angles would be 0.2°. Also for example, if the scanning device generates groups of scan data at 1,200 angles that range from 0 to 360° and that are evenly spaced, then the increment between angles would be 0.3°.

Figure 2:
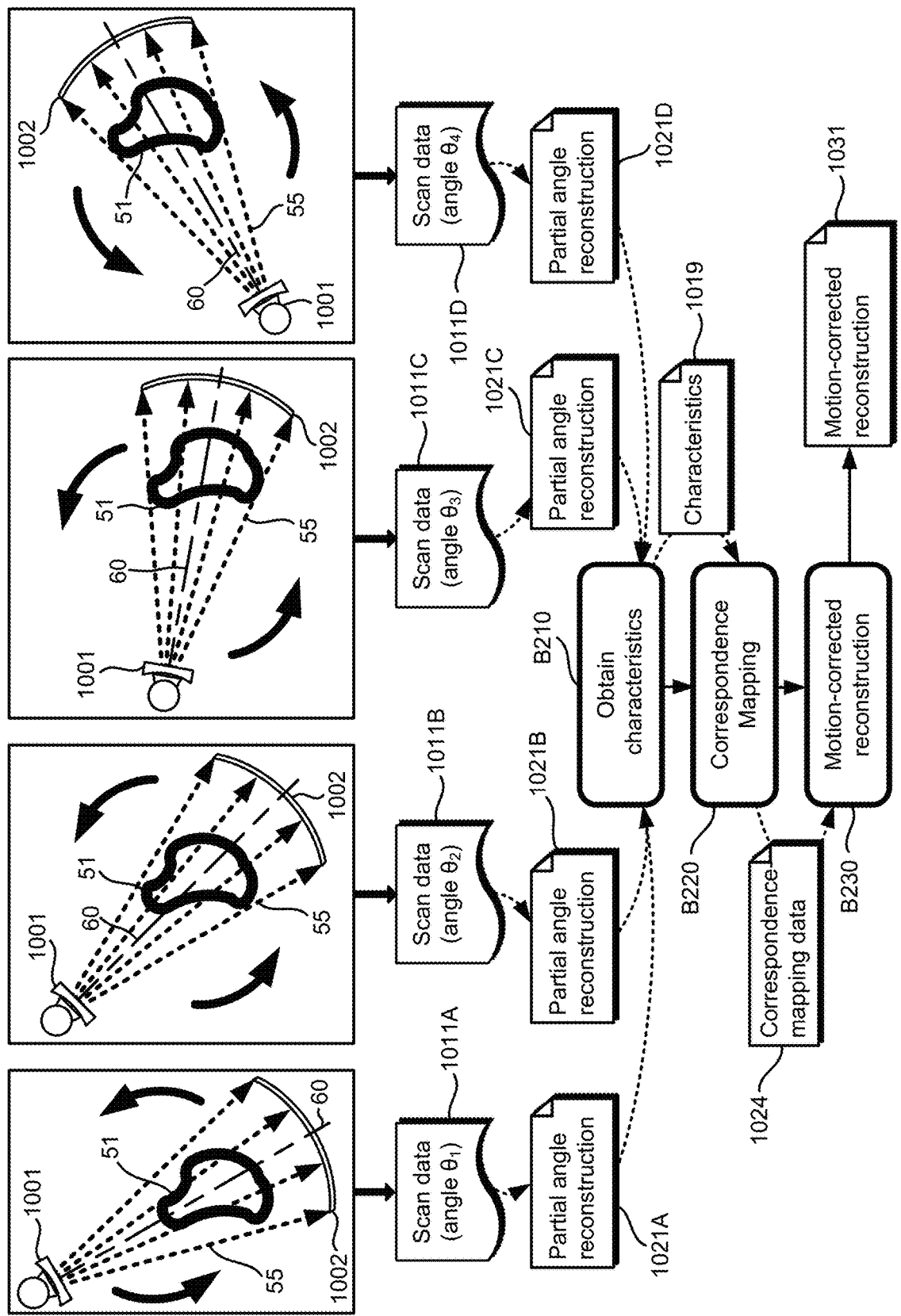
FIG. 2 illustrates an example embodiment of the flow of information in a medical-imaging system.

FIG. 2 illustrates an example embodiment of the flow of information in a medical-imaging system. The system includes a radiation emitter 1001 and a radiation detector 1002, which are positioned on opposite sides of a subject 51. The radiation emitter 1001 emits radiation 55 (e.g., x-rays) that travels through a scanned region of the subject 51 and is detected by the radiation detector 1002. The radiation detector 1002 generates groups of scan data 1011 based on the detected radiation 55.

For example, in FIG. 2, the scan data in a first group of scan data 1011A were generated based on radiation that was emitted and detected while an axis 60 between the radiation emitter 1001 and the radiation detector 1002 was at angle $\theta_1$. Also for example, the scan data in a second group of scan data 1011B were generated based on radiation that was emitted and detected while an axis 60 between the radiation emitter 1001 and the radiation detector 1002 was at angle $\theta_2$.

Furthermore, in some embodiments, a group of scan data 1011 is generated based on radiation that was emitted and detected over a range of angles. For example, in some embodiments, a group of scan data 1011 is generated based on radiation that was emitted and detected over an angular range of 0.6°. As used herein, the detection angle of a group of scan data 1011 (or of a PAR 1021) refers to a single angle or a range of angles at which the radiation was emitted and detected. And the detection angle of a group of scan data 1011 may overlap with the detection angle of one or more other groups of scan data 1011. For example, the detection angle of the second group of scan data 1011B may overlap with one or both of the detection angles of the first group of scan data 1011A and the third group of scan data 1011C.

Next, PARs 1021 of the scanned region are generated based on the groups of scan data 1011. Each of the PARs 1021 includes one or more respective images (PAR images). As noted above, examples of reconstruction processes include filtered back projection and iterative reconstruction. In the embodiment in FIG. 2, a first PAR 1021A is generated based on the first group of scan data 1011A, a second PAR 1021B is generated based on a second group of scan data 1011B, a third PAR 1021C is generated based on a third group of scan data 1011C, and a fourth PAR 1021D is generated based on a fourth group of scan data 1011D.

Additionally, if an object (the subject or a part of the subject) was moving as the radiation emitter 1001 and the radiation detector 1002 were emitting radiation and generating scan data (e.g., the object changed its position as the radiation emitter 1001 and the radiation detector 1002 moved to new positions), then the positions of the object may be different in one or more of the PARs 1021. Accordingly, a full (angle) reconstruction based on the PARs 1021 may include blurring or other artifacts.

In block B210, one or more respective characteristics 1019 of the PARs 1021 are obtained. The characteristics 1019 may include respective metadata (e.g., the detection angle) of the PARs 1021, the respective streak angles of the PARs 1021, a feature's respective locations (e.g., a vessel center, a center of trachea) in the PARs 1021, and a path that was traveled by an object or a feature in the PARs 1021.

Next, in B220, correspondence mapping is performed on the PARs 1021 based on the characteristics 1019 and on the PARs 1021. In some embodiments, performing the correspondence mapping includes performing one or more transformations (e.g., a rotation, a translation) or performing image registration. The correspondence mapping in B220 outputs correspondence-mapping data 1024. Examples of correspondence-mapping data 1024 include alignment data and motion maps (e.g., warping fields).

Then, in B230, motion-corrected-reconstruction operations are performed based on the correspondence-mapping data 1024 and on the scan data 1011, the PARs 1021, or both the scan data 1011 and the PARs 1021. The motion-corrected-reconstruction operations in block B230 output a motion-corrected reconstruction 1031.

Figure 3:
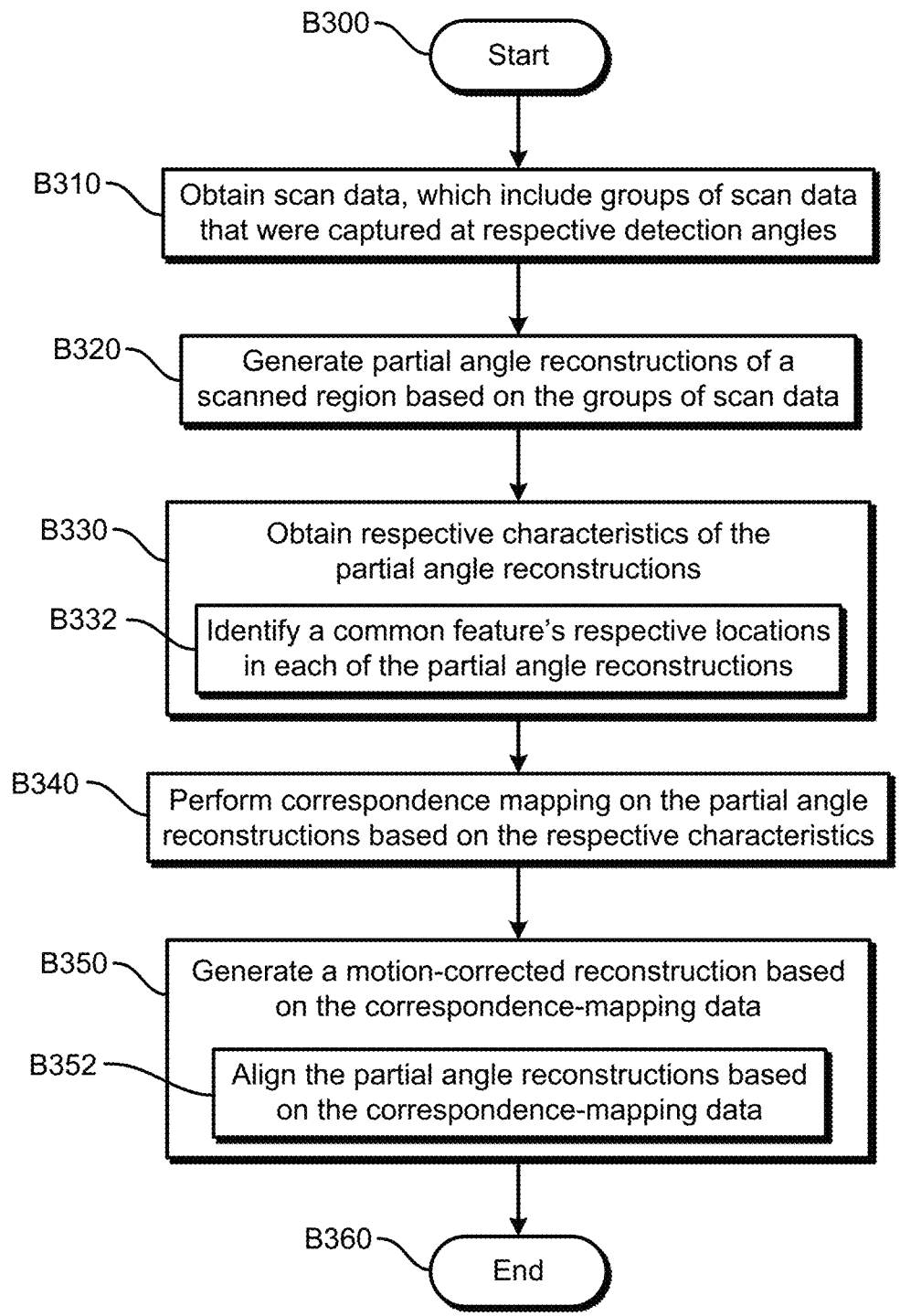
FIG. 3 illustrates an example embodiment of an operational flow for generating a motion-corrected reconstruction.

FIG. 3 illustrates an example embodiment of an operational flow for generating a motion-corrected reconstruction. Although this operational flow and the other operational flows that are described herein are each presented in a certain order, some embodiments may perform at least some of the operations in different orders than the presented orders. Examples of different orders include concurrent, parallel, overlapping, reordered, simultaneous, incremental, and interleaved orders. Thus, other embodiments of the operational flows that are described herein may omit blocks, add blocks, change the order of the blocks, combine blocks, or divide blocks into more blocks. For example, in some embodiments of FIG. 3, block B340 includes the operations that are included in block B1220 in FIG. 12.

Furthermore, although this operational flow and the other operational flows that are described herein are performed by an image-generation device, some embodiments of these operational flows are performed by two or more image-generation devices or by one or more other specially-configured computing devices.

The flow begins in block B300 and moves to block B310, where an image-generation device obtains scan data, which include groups of scan data that were captured at respective detection angles. Next, in block B320, the image-generation device generates PARs of a scanned region based on the groups of scan data. Each of the PARs is generated based on one or more respective groups of the groups of scan data. Also, in some embodiments, each group of scan data is used during the generation of one, and only one, PAR.

Figure 4:
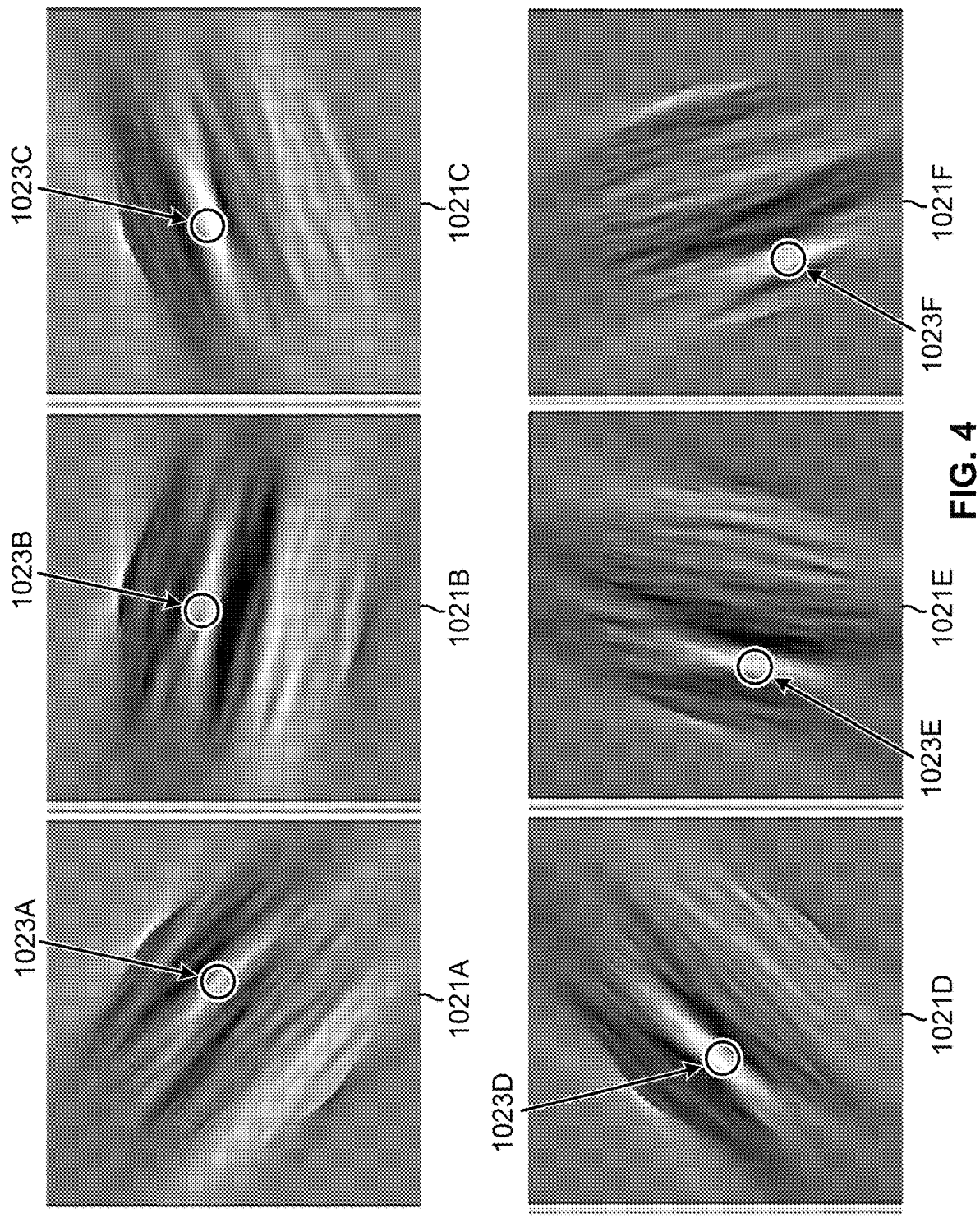
FIG. 4 illustrates example embodiments of partial angle reconstructions (PARs) and the respective locations of a common feature in each of the PARs.

The flow then proceeds to block B330, where the image-generation device obtains respective characteristics of the PARs. In FIG. 3, block B330 includes block B332. In block B332, the image-generation device identifies a common feature's respective locations in each of the PARs. The common feature is a feature that is common to (found in) each of the PARs. FIG. 4 illustrates example embodiments of PARs 1021 and the respective locations 1023 of a common feature in each of the PARs. In this example, the common feature is a vessel (e.g., artery, vein) or trachea. Also, using a common feature that is easily distinguished from the rest of the PAR may make finding the common feature's respective locations easier. In FIG. 4, the vessel carries a contrast agent, which helps to distinguish the vessel from the other parts of the PAR.

FIG. 4 shows the vessel's respective location 1023A in a first PAR 1021A, shows the vessel's respective location 1023B in a second PAR 1021B, and shows the vessel's respective location 1023C in a third PAR 1021C. Because the vessel was moving during the generation of the scan data, the respective locations 1023 in the PARs 1021 are different. Thus, the respective locations 1023 of the common feature are located at different coordinates in each of the PARs 1021.

Some embodiments of the anomaly-detection device identify the location of a feature in a PAR by selecting the pixel or voxel in the PAR that has the highest or maximum Hounsfield unit (HU) value, by searching for the mass center of the feature, or by using a profile along a normal direction (parallel to the scan range). And some embodiments of the anomaly-detection device use other methods, such as other stable analytical methods or machine-learning methods (e.g., neural networks), to identify the location of a feature in a PAR.

Next, in block B340, the image-generation device performs correspondence mapping on the PARs and generates correspondence-mapping data thereby. For example, the image-generation device may determine the relative locations of the common feature in the PARs, and the correspondence-mapping data may indicate the relative locations. For example, the correspondence-mapping data may include translations that can be performed on the PARs to bring the respective locations of the common feature into alignment. In an example of one such embodiment, the correspondence-mapping data include translations that can be performed to align the locations 1023B-F in the second through sixth reconstructions 1021B-F with the location 1023A in the first reconstruction 1021A.

Figure 5:
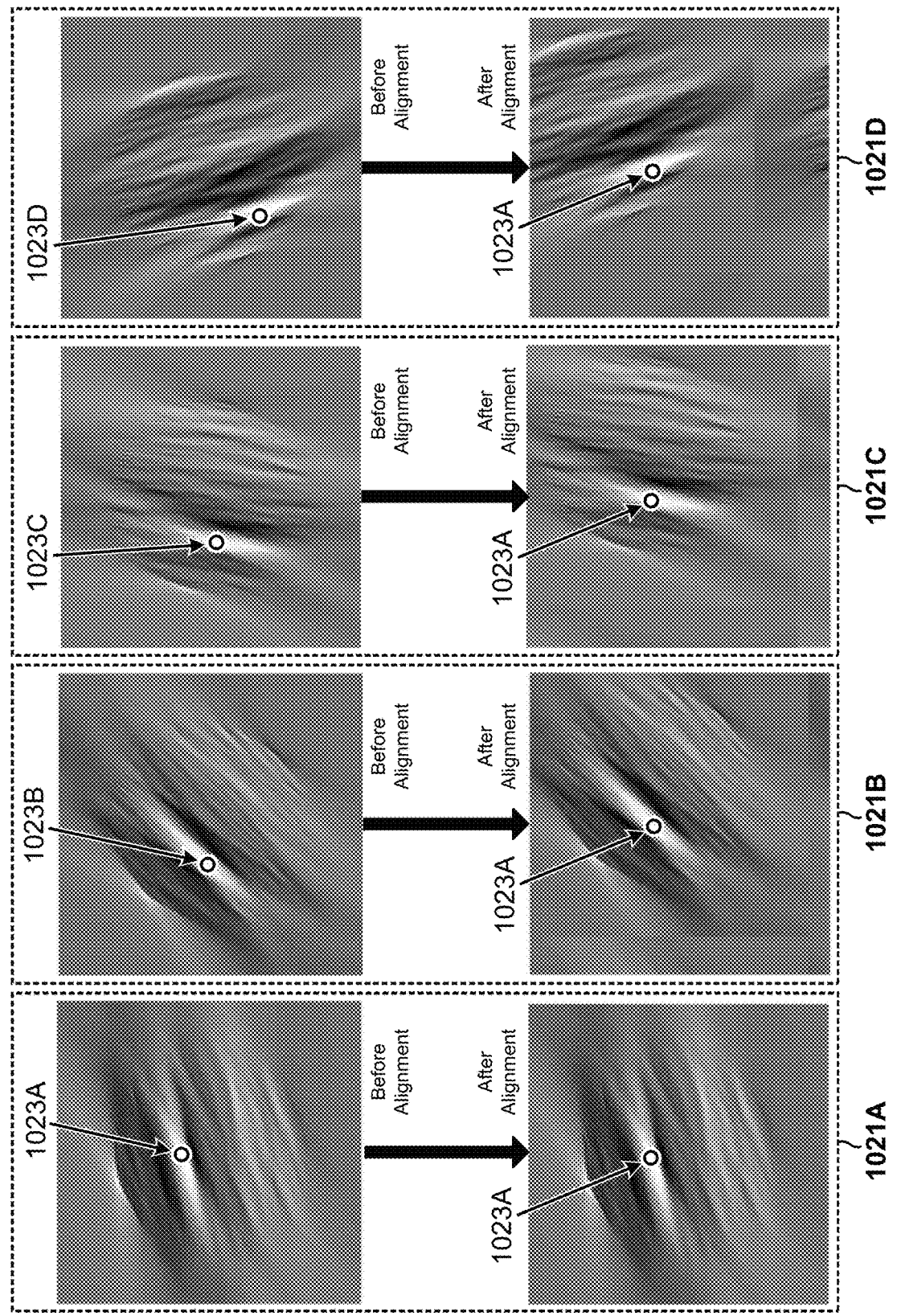
FIG. 5 illustrates example embodiments of aligned partial angle reconstructions (PARs) and the respective locations of a common feature in each of the PARs.

Then, in block B350, the image-generation device generates a motion-corrected reconstruction based, in part, on the correspondence-mapping data. Block B350 includes block B352, in which the image-generation device aligns the PARs based on the correspondence-mapping data. FIG. 5 illustrates example embodiments of aligned PARs 1021 and the respective locations 1023 of a common feature in each of the PARs. In FIG. 5, the second, third, and fourth PARs 1021B-D are aligned to the first PAR 1021A. Consequently, the location 1023A of the common feature in the first PAR 1021A is not change by the alignment, but the other locations 1023B-D of the common feature in the second, third, and fourth PARs 1021B-D are changed by the alignment. Also, after the aligning, the locations 1023A-D can be described with the same coordinates. The image-generation device then generates the motion-corrected reconstruction based on the aligned PARs and, in some embodiments, on the scan data. Lastly, the flow ends in block B360.

Figure 6:
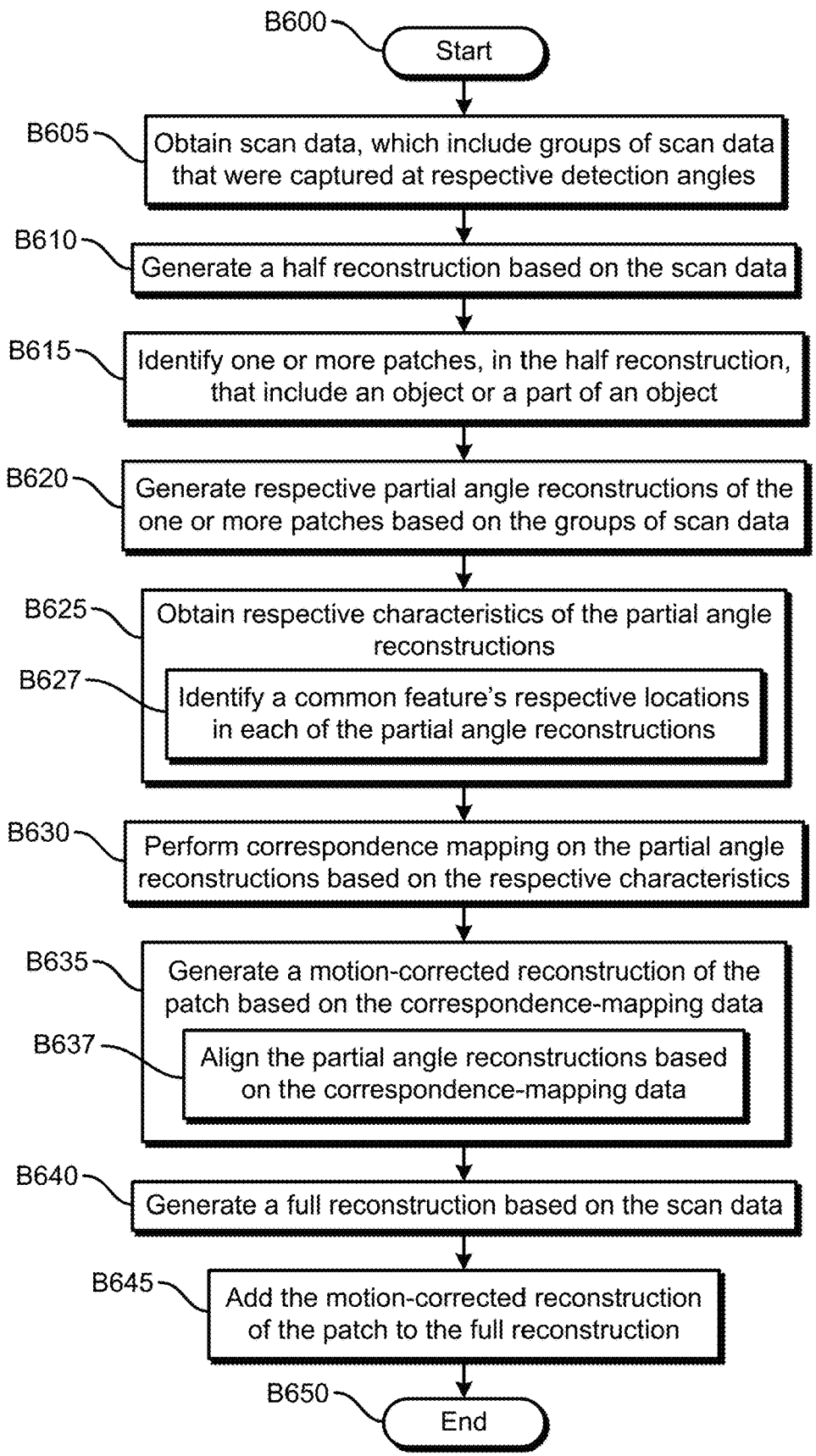
FIG. 6 illustrates an example embodiment of an operational flow for generating a motion-corrected reconstruction.

FIG. 6 illustrates an example embodiment of an operational flow for generating a motion-corrected reconstruction. The flow starts in block B600 and then moves to block B605, where an image-generation device obtains scan data, which include groups of scan data that were captured at respective detection angles. Next, in block B610, the image-generation device generates a half reconstruction based on the scan data. In some embodiments, the image generation device generates a full reconstruction (or other reconstruction).

Figure 7A:
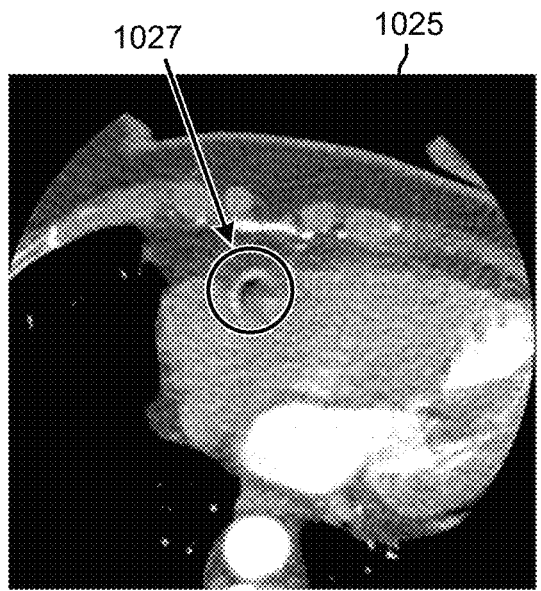
FIG. 7A illustrates an example embodiment of a half reconstruction.
Figure 7B:
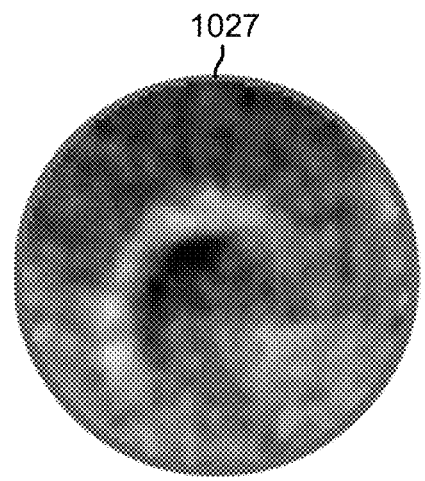
FIG. 7B illustrates the patch from FIG. 7A.

The flow then moves to block B615, where the image-generation device identifies one or more patches, in the half reconstruction, that include an object or a part of an object. For example, FIG. 7A illustrates an example embodiment of a half reconstruction 1025. Also, FIG. 7A illustrates a patch 1027 that includes an object or a part of an object. In this embodiment, the object is a vessel (e.g., a right coronary artery). FIG. 7B illustrates the patch 1027 from FIG. 7A.

Figure 7C:
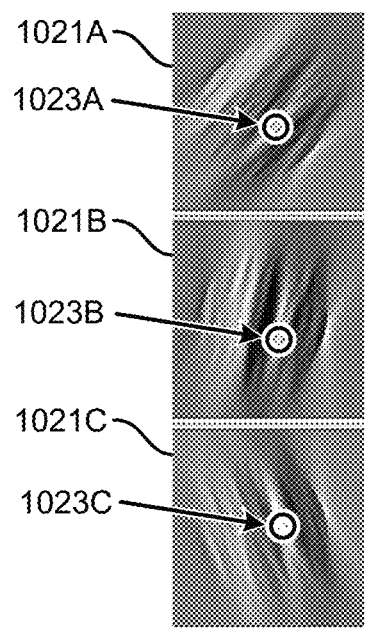
FIG. 7C illustrates partial angle reconstructions (PARs) of the patch in FIG. 7B.

Next, in block B620, the image-generation device generates PARs of the patch based on the groups of scan data. Each of the PARs is generated based on one or more respective groups of the groups of scan data. Also, in some embodiments, each group of scan data is used during the generation of one, and only one, PAR. For example, FIG. 7C illustrates PARs of the patch in FIG. 7B.

The flow then proceeds to block B625, where the image-generation device obtains respective characteristics of the PARs. Block B625 includes block B627. In block B627, the image-generation device identify a common feature's respective locations in each of the PARs. For example, in FIG. 7C, the common feature is the center of the vessel. FIG. 7C shows the vessel center's respective locations 1023 in the PARs 1021. Because the vessel was moving during the generation of the scan data, the respective locations 1023 in the PARs 1021 are different. Thus, the respective locations 1023 are located at different coordinates in each of the PARs 1021.

The flow then moves to block B630, where the image-generation device performs correspondence mapping on the PARs based on the respective characteristics and generates correspondence-mapping data (e.g., data that define one or more translations (or other transformations)).

Next, in block B635, the image-generation device generates a motion-corrected reconstruction of the patch based on the correspondence-mapping data. Block B635 includes block B637, in which the image-generation device aligns (e.g., performs one or more translations on) the PARs based on the correspondence-mapping data.

Then, in block B640, the image-generation device generates a full reconstruction based on the scan data. The flow then moves to block B645, where the image-generation device adds the motion-corrected reconstruction of the patch to the full reconstruction. The image-generation device may perform feathering or interpolation operations, for example to blend the motion-corrected reconstruction of the patch into the full reconstruction.

Additionally, some embodiments eliminate B640 and use the half reconstruction instead of the full reconstruction in block B645.

Finally, the flow ends in block B650.

Figure 8:
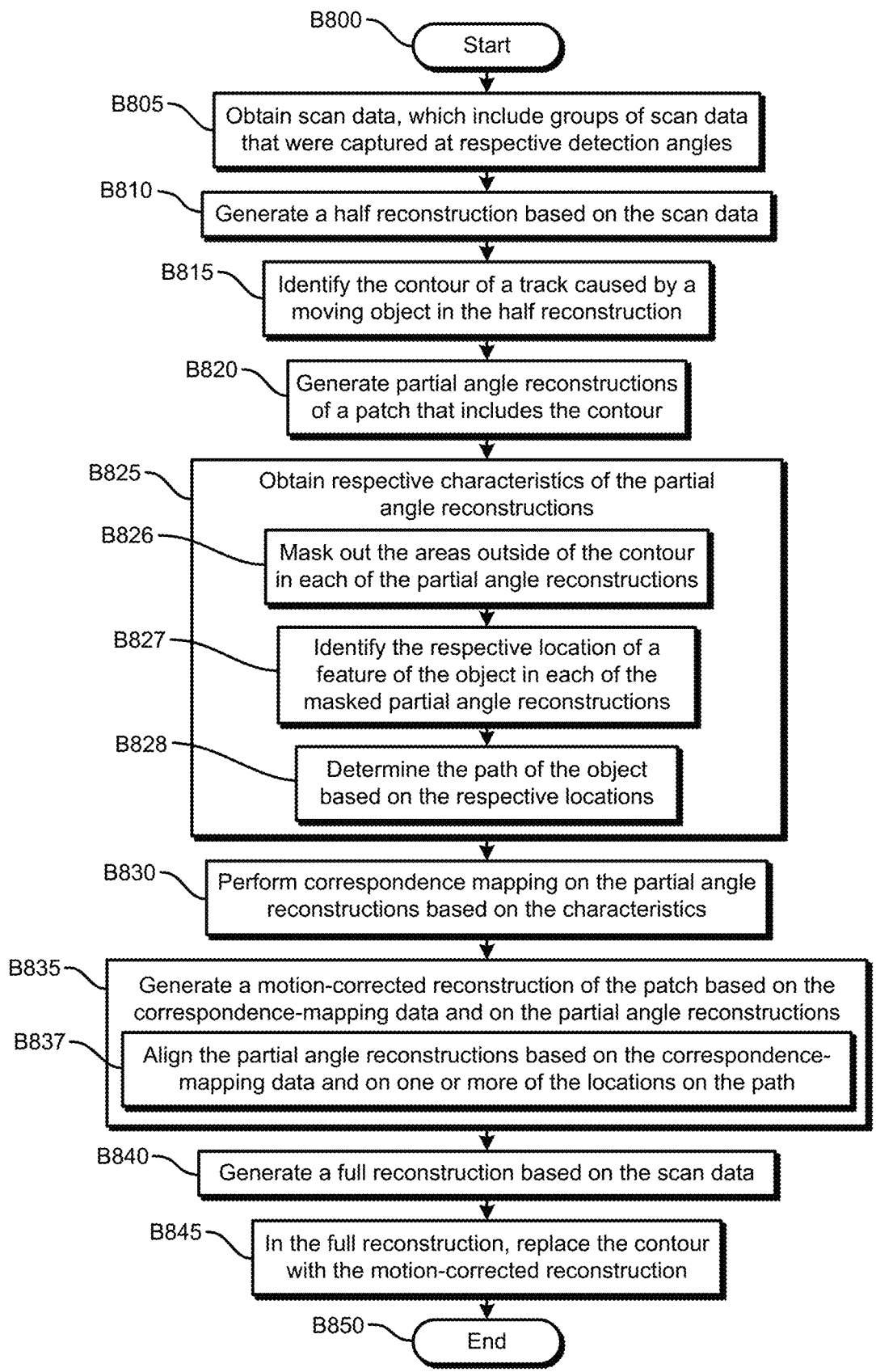
FIG. 8 illustrates an example embodiment of an operational flow for generating a motion-corrected reconstruction.

FIG. 8 illustrates an example embodiment of an operational flow for generating a motion-corrected reconstruction. The flow starts in block B800 and then moves to block B805, where an image-generation device obtains scan data, which include groups of scan data that were captured at respective detection angles. Next, in block B810, the image-generation device generates a half reconstruction based on the scan data.

Figure 9A:
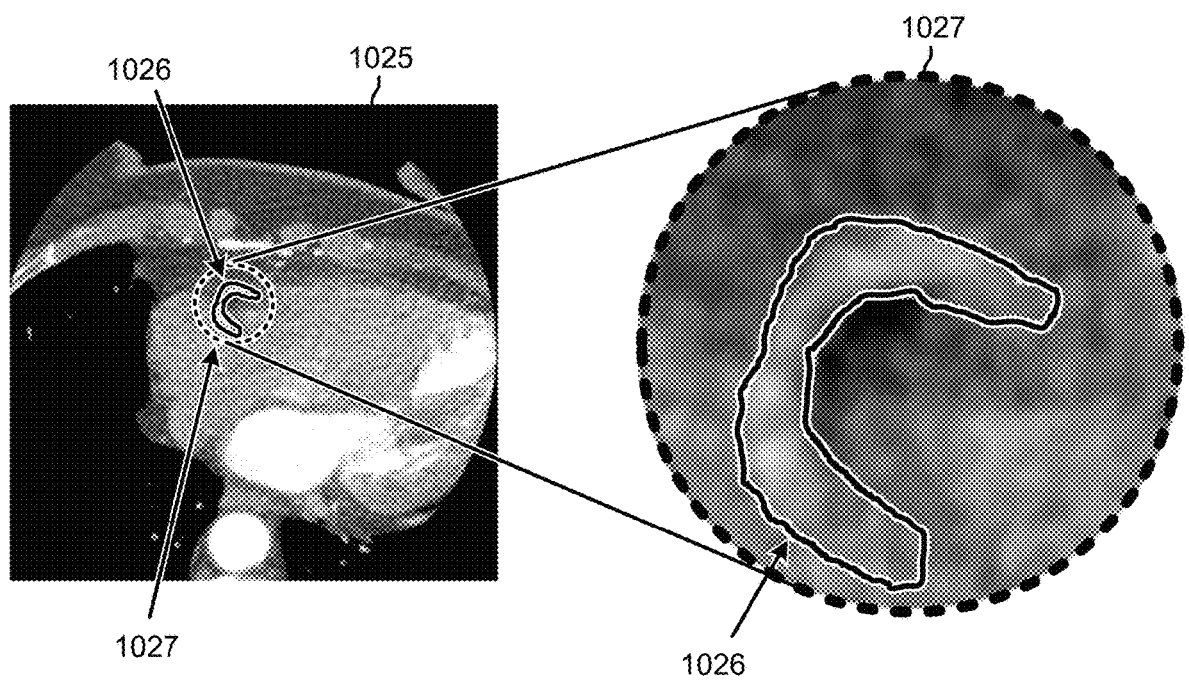
FIG. 9A illustrates an example embodiment of a contour of a track caused by a moving object.

The flow then proceeds to block B815, where the image-generation device identifies, in the half reconstruction, the contour of a track caused by a moving object (e.g., an object that moved during the capture of a group of scan data or between the capture of two or more groups of scan data). For example, the contour may be identified using one or more machine-learning models (e.g., deep neural networks). The contour outlines an area (in two dimensions) or a volume (in three dimensions) in which the object moved. In some embodiments, the contour is defined such that no part of the moving object is outside of the contour. For example, FIG. 9A illustrates an example embodiment of a contour 1026 of a track caused by a moving object. In this example, the object is a vessel, and the contour 1026 delineates the area in the half reconstruction 1025 in which the vessel moved during the capture of the scan data.

Next, in block B820, the image-generation device generates PARs of a patch that includes the contour. For example, FIG. 9A illustrates a patch 1027 that includes the contour 1026.

The flow then moves to block B825, where the image-generation device obtains respective characteristics of the PARs. Block B825 includes blocks B826-B828. In block B826, the image-generation device uses the contour as a mask to mask out the areas (or volumes) that are outside of the contour in each of the PARs. Then, in block B827, the image-generation device identifies the respective location of a feature of the object in each of the masked PARs. The masking of the non-contour area helps to eliminate false positives of the feature. For example, if the object has a high contrast and the feature is a pixel or voxel that has the maximum HU value, then the masking will prevent the image-generation device from identifying the location of a pixel or voxel that is outside of the contour and that has the maximum HU value.

Figure 9B:
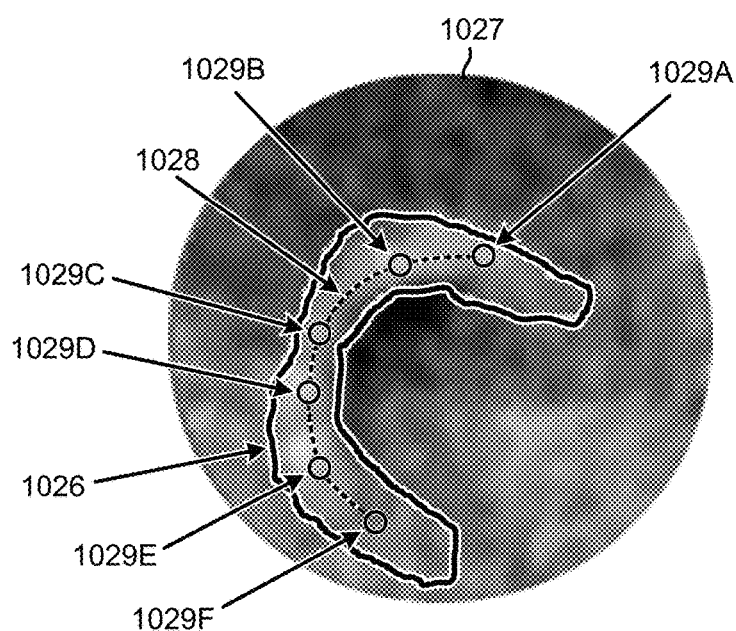
FIG. 9B illustrates an example embodiment of a path of an object in the contour of FIG. 9A.

Next, in block B828, the image-generation device determines the path of the object based on the respective locations. For example, the image-generation device may identify where the locations of the feature are in the contour and the temporal order in which the feature visited these locations and then generate a path that travels through the locations (e.g., that connects the locations). Block B828 may include one or more smoothing operations. FIG. 9B illustrates an example embodiment of a path of an object in the contour of FIG. 9A. The path 1028 includes locations 1029A-F, which correspond to the locations 1023A-F of the feature in FIG. 7C. Also, the alphabetic order A-F indicates the temporal order in which the feature visited these locations during the capture of the scan data. For example, the feature visited location 1029C before it visited location 1029D, and the feature visited location 1029D before it visited location 1029E.

The flow then advances to block B830, where the image-generation device performs correspondence mapping on the PARs based on the characteristics and generates correspondence-mapping data.

Next, in block B835, the image-generation device generates a motion-corrected reconstruction of the patch based on the correspondence-mapping data and on the PARs. Block B835 includes block B837, in which the image-generation device aligns the PARs based on the correspondence-mapping data and on one or more of the locations on the path. For example, the image-generation device may use one location in a PAR as a fixed location and align the other PARs such that the other locations are aligned to the fixed location. Also for example, the image-generation device may use location 1029D in FIG. 9B as a fixed location and align the PARs such that the other locations (1029A-C, 1029E-F) are aligned with location 1029D. The image-generation device may allow a user to select the fixed location, and the image-generation device may select the fixed location without user input.

Figure 10:
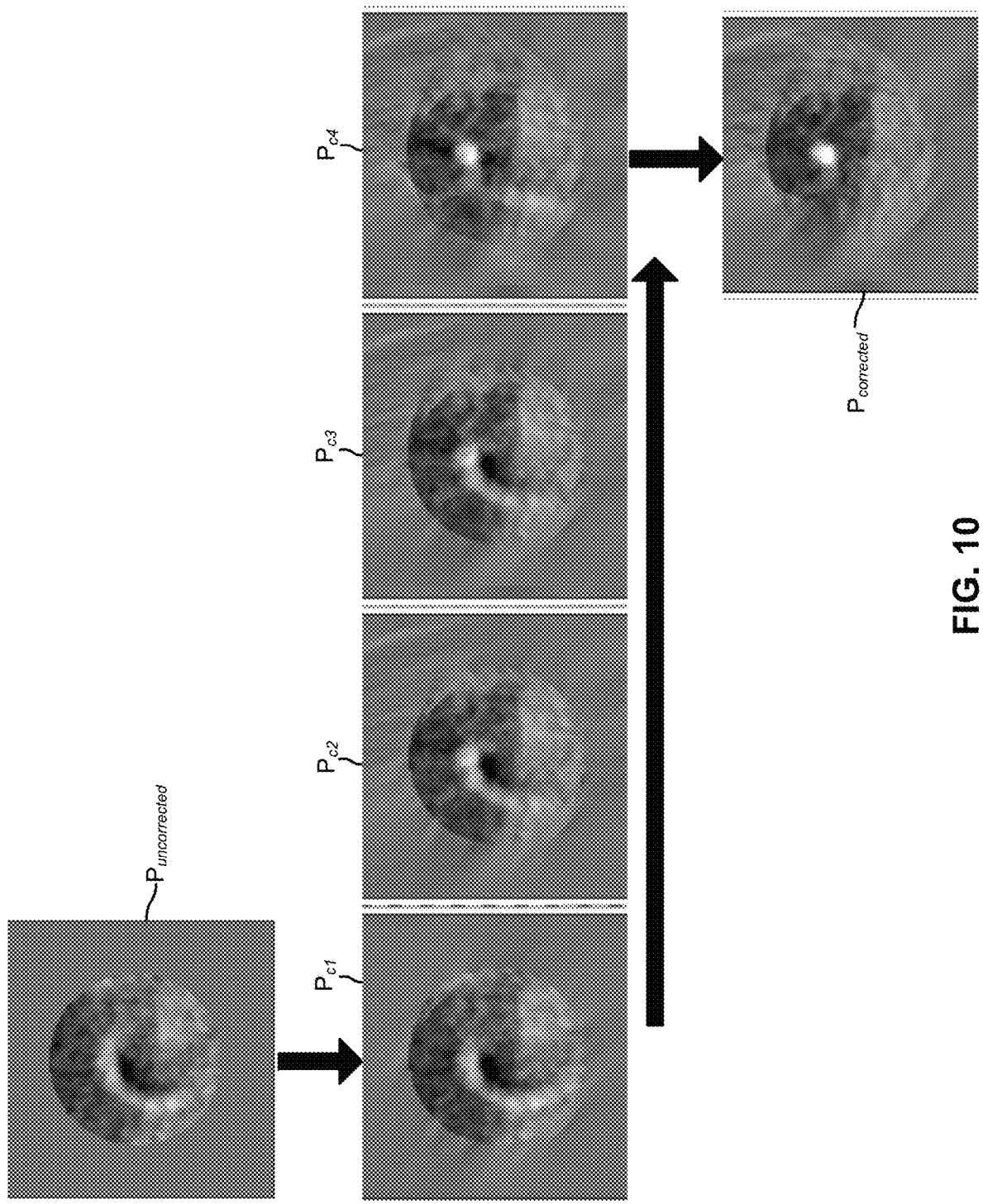
FIG. 10 illustrates an example embodiment of the generation of a motion-corrected reconstruction of a patch.

Additionally, some embodiments of the image-generation device generate the motion-corrected reconstruction of the patch by summing the aligned PARs. For example, FIG. 10 illustrates an example embodiment of the generation of a motion-corrected reconstruction of a patch. $P_{uncorrected}$ is an initial uncorrected reconstruction of the patch. Six PARs of the patch were generated, the location of a feature in one of the PARs was selected as a fixed location, and the other five PARs were aligned such that their feature locations are aligned with the fixed location. $P_{c1}$ is a reconstruction of the patch in which one of the other five PARs has been aligned such that its feature location is aligned with the fixed location. $P_{c2}$ is a reconstruction of the patch in which two of the other five PARs have been aligned such that their feature locations are aligned with the fixed location. $P_{c3}$ is a reconstruction of the patch in which three of the other five PARs have been aligned such that their feature locations are aligned with the fixed location. $P_{c4}$ is a reconstruction of the patch in which four of the other five PARs have been aligned such that their feature locations are aligned with the fixed location. Finally, $P_{corrected}$ is a reconstruction of the patch in which all five of the other PARs have been aligned such that their feature locations are aligned with the fixed location.

As shown by FIG. 10, the motion blur of the object (an artery in this example) is further reduced each time another PAR is aligned. In $P_{corrected}$, the object is in focus. Thus, the generation of the motion-corrected reconstruction of the patch may be a refocusing operation.

From block B835, the flow moves to block B840, where the image-generation device generates a full reconstruction based on the scan data. Next, in block B845, the image-generation device replaces the contour (or the patch) in the full reconstruction with the motion-corrected reconstruction of the contour (or the patch). The image-generation device may perform feathering or interpolation to blend the motion-corrected reconstruction of the contour (or the patch) into the full reconstruction. Also, the motion-corrected reconstruction of the contour (or the patch) may be aligned with the full reconstruction such that the fixed location to which the PAR were aligned in block B837 is aligned to the fixed location in the full reconstruction. For example, if in block B837 the PARs are aligned to location 1029B in FIG. 9B, then the motion-corrected reconstruction of the contour (or the patch) may be added to the full reconstruction such that location 1029B in the motion-corrected reconstruction of the contour (or the patch) is aligned to location 1029B in the full reconstruction.

Then the flow ends in block B850.

Also, some embodiments use the half reconstruction in block B845 and omit block B840. And some embodiments generate the full reconstruction in block B810 and omit block B840.

Figure 11:
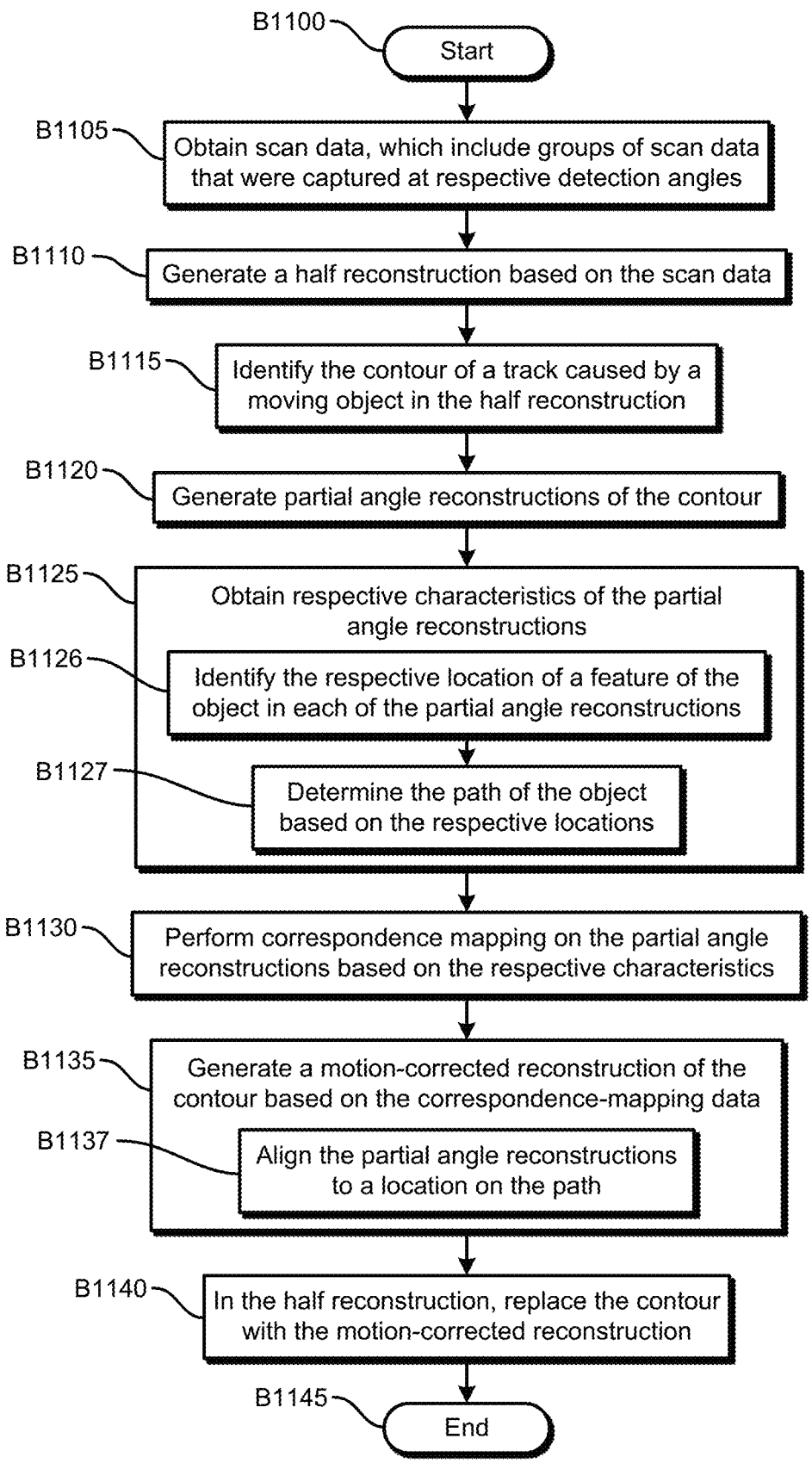
FIG. 11 illustrates an example embodiment of an operational flow for generating a motion-corrected reconstruction.

FIG. 11 illustrates an example embodiment of an operational flow for generating a motion-corrected reconstruction. The flow starts in block B1100 and then moves to block B1105, where an image-generation device obtains scan data, which include groups of scan data that were captured at respective detection angles. Next, in block B1110, the image-generation device generates a half reconstruction based on the scan data.

The flow then proceeds to block B1115, where the image-generation device identifies, in the half reconstruction, the contour of a track caused by a moving object (e.g., an object that moved during the capture of a group of scan data or between the capture of two or more groups of scan data).

Next, in block B1120, the image-generation device generates PARs of the contour.

The flow then moves to block B1125, where the image-generation device obtains respective characteristics of the PARs. Block B1125 includes blocks B1126-B1127. In block B1126, the image-generation device identifies the respective location of a feature of the object in each of the PARs of the contour. Next, in block B1127, the image-generation device determines the path of the object based on the respective locations. Block B1127 may include one or more smoothing operations.

Then the flow proceeds to block B1130, where the image-generation device performs correspondence mapping on the PARs based on the respective characteristics. Next, in block B1135, the image-generation device generates a motion-corrected reconstruction of the contour based on the correspondence-mapping data. Block B1135 includes block B1137, in which the image-generation device aligns the PARs to a location on the path based on the correspondence-mapping data.

Then the flow proceeds to block B1140, where the image-generation device replaces the contour in the half reconstruction with the motion-corrected reconstruction of the contour. Then the flow ends in block B1145.

Also, in some embodiments, the image-generation device generates a full reconstruction in block B1110 and uses the full reconstruction in block B1140. And in some embodiments, the image-generation device generates a full reconstruction in block B1140 and replaces the contour in the full reconstruction with the motion-corrected reconstruction of the contour.

Figure 12:
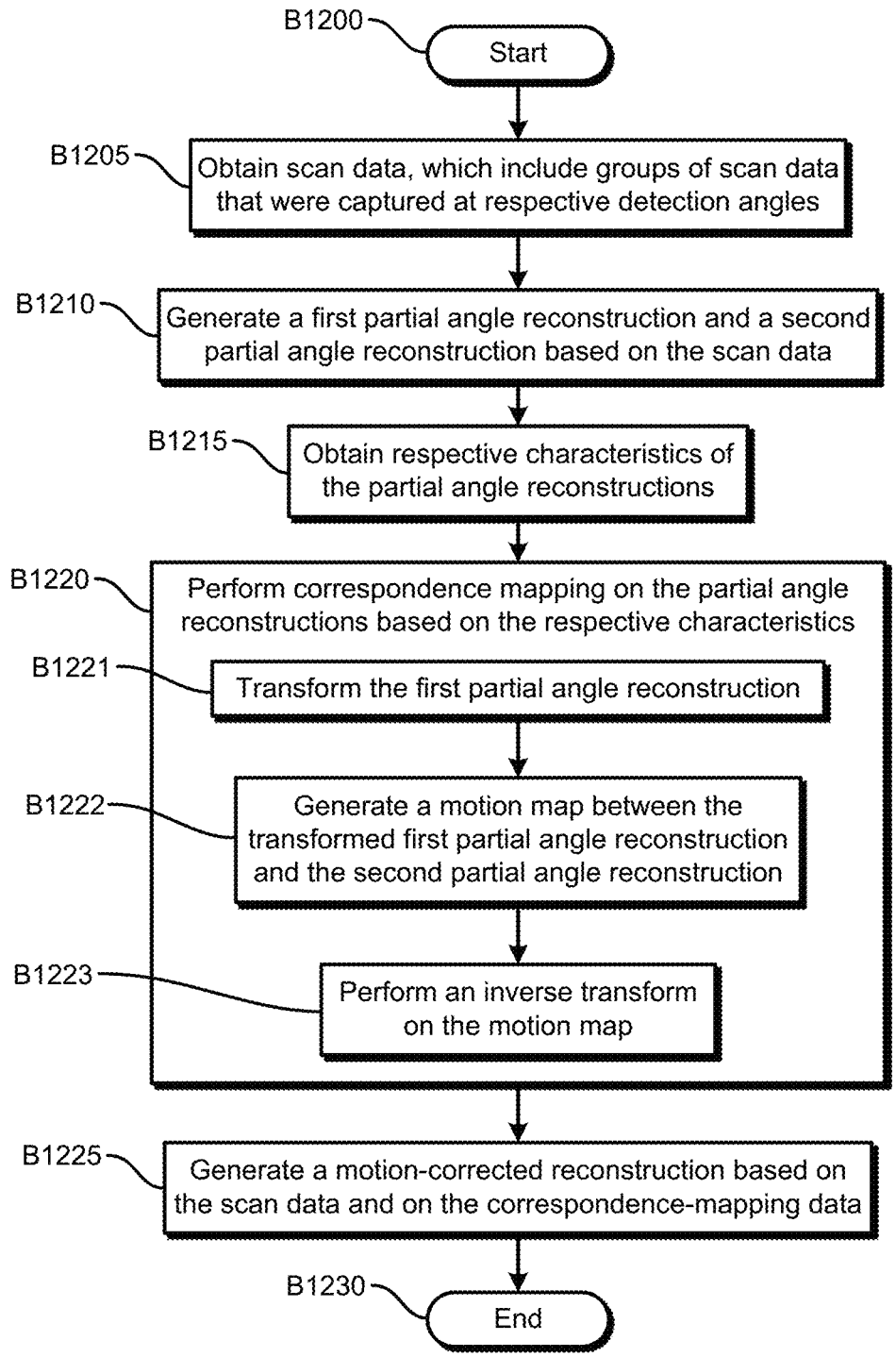
FIG. 12 illustrates an example embodiment of an operational flow for generating a motion-corrected reconstruction.
Figure 13:
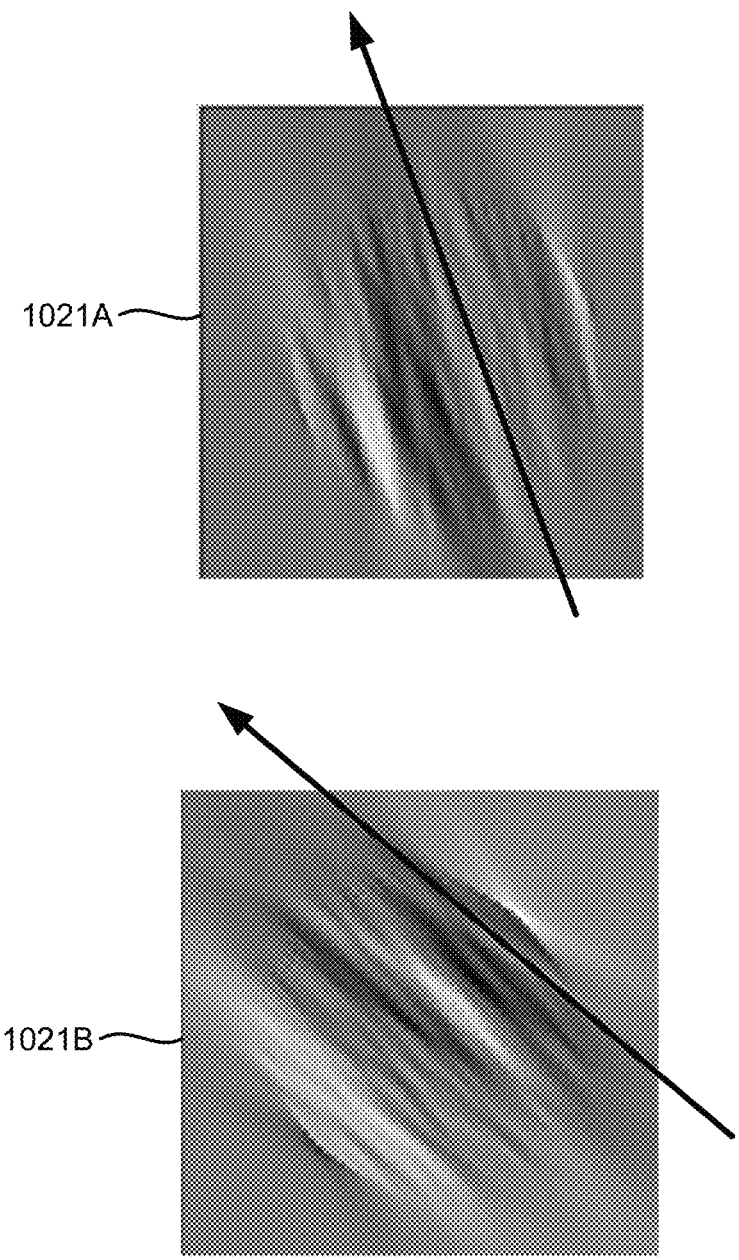
FIG. 13 illustrates examples of partial angle reconstructions (PARs) that include streak artifacts.

FIG. 12 illustrates an example embodiment of an operational flow for generating a motion-corrected reconstruction. The flow begins in block B1200 and moves to block B1205, where the image-generation device obtains scan data, which include groups of scan data that were captured at respective detection angles. Next, in block B1210, the image-generation device generates a first PAR and a second PAR based on the scan data. PARs may include artifacts, such as streak artifacts. For example, FIG. 13 illustrates examples of PARs that include streak artifacts. The streak directions in the PARs 1021 are indicated by the arrows. The streak artifacts may degrade registration between the PARs and introduce false results into a motion map.

After block B1210, the flow proceeds to block B1215, where the image-generation device obtains respective characteristics of the PARs. In this embodiment, the characteristics include the respective detection angles of the first and second PARs or include the streak directions in the first and second PARs. For example, the respective detection angles may be obtained from metadata that accompanies the scan data, and the streak directions may be obtained from an analysis of the first and second PARs.

Next, in block B1220, the image-generation device performs correspondence mapping on the PARs based on the respective characteristics. Block B1220 includes blocks B1221-B1223.

In block B1221, the image-generation device transforms the first PAR based on the respective characteristics. In some embodiments, the transformation is an affine transformation or another invertible transformation. In the following example, the transformation is a rotation. For example, if the first PAR was generated based on scan data that were captured at detection angle $\theta_1$ (which is an example of a respective characteristic) and the second PAR was generated based on scan data that were captured at detection angle $\theta_2$ (which is an example of a respective characteristic), then the first PAR may be transformed (rotated by) a rotation angle $\theta_r$ that equals their difference ($\theta_r = \theta_2 - \theta_1$). Also, instead of rotating the first PAR, the second PAR can be transformed (rotated by) a rotation angle $\theta_r$ that equals their difference ($\theta_r = \beta_1 - \theta_2$).

Next, in block B1222, the image-generation device generates a motion map (e.g., a warping field) between the transformed first PAR and the second PAR (the non-transformed PAR). A motion map includes a respective motion value (e.g., motion vector) for one or more of the points (e.g., each point) or regions in the PARs. For example, a motion map may include a respective motion vector for each pixel, pixel region (a group of two or more contiguous pixels), voxel, or voxel region (a group of two or more contiguous voxels). Block B1222 may include image registration. Some embodiments use an iterative search method, such as free-form deformation with B-spline and optical flow, to generate the motion map. And some embodiments use one or more deep-learning architectures, for example deep neural networks, deep belief networks, recurrent neural networks, and convolutional neural networks. The flow then moves to block B1223, where the image-generation device performs an inverse transform (an inverse of the transform that was performed in block B1221) on the motion map. Also, the generated correspondence-mapping data include the transformed motion map (which includes a respective motion value (e.g., motion vector) for one or more of the points or regions in the PARs).

Figure 14:
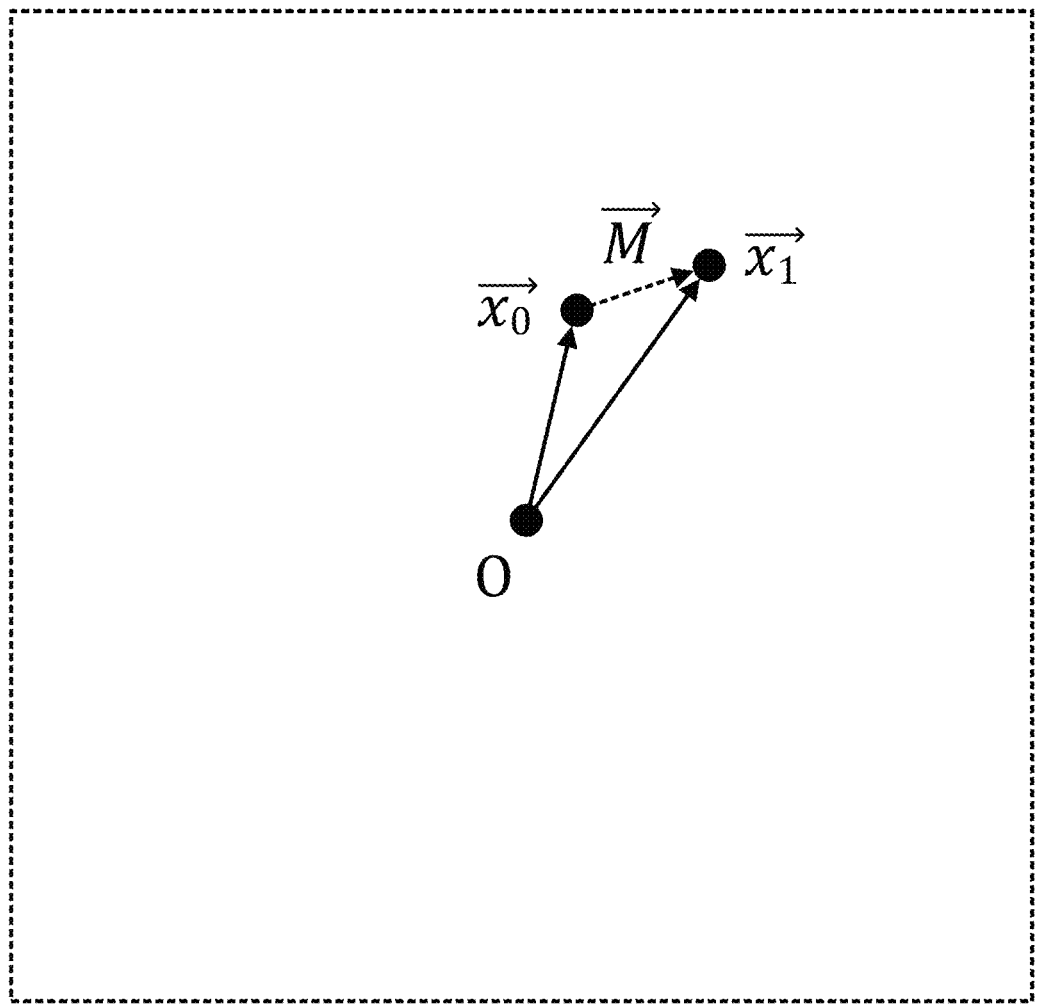
FIG. 14 illustrates an example of a point in an object that moved during the capture of scan data.

For example, FIG. 14 illustrates an example of a point in an object that moved during the capture of scan data. In FIG. 14, $\vec{x}_0$ is the location of the point at time $t_0$, motion vector $\vec{M}$ is the motion of the point between time $t_0$ and time $t_1$, and $\vec{x}_1$ is the location of the point at time $t_1$. Thus, $$\vec{x}_1 = \vec{x}_0 + \vec{M}. \tag{1}$$

Figure 15:
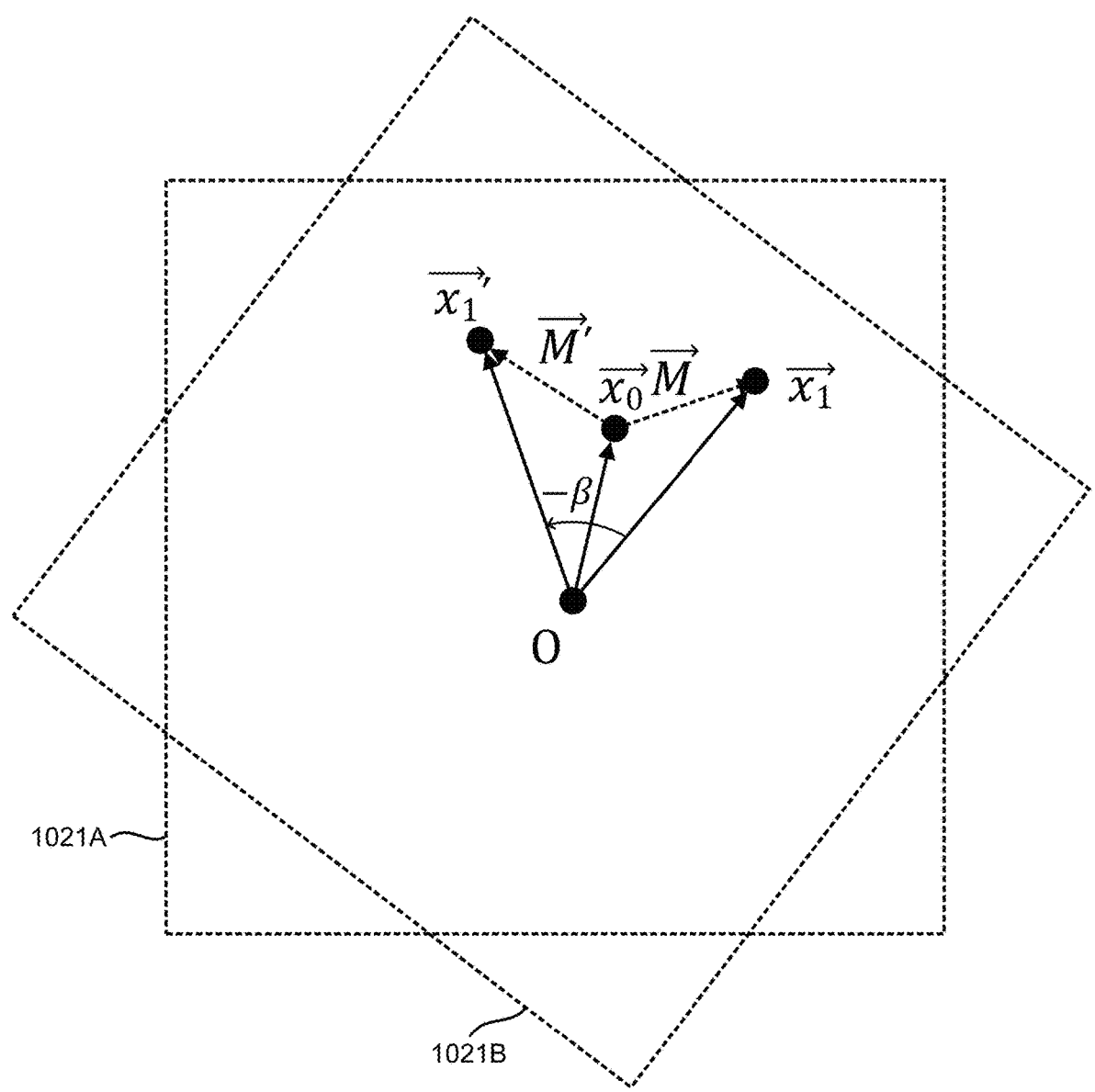
FIG. 15 illustrates an example of a transformation of the point in FIG. 14.

FIG. 15 illustrates an example of a transformation of the point in FIG. 14. In FIG. 15, the transformation is a rotation, and angle is the difference between the detection angle at time $t_0$ and time $t_1$. The PAR 1021B that includes the point at location $\vec{x}_1$ was rotated by $-\beta$ relative to the PAR 1021A that includes the point at location $\vec{x}_0$. Therefore, the point in PAR 1021B moves from location $\vec{x}_1$ to $\vec{x}_1'$. Accordingly, $$\vec{x}_1' = \vec{x}_0 + \vec{M}'. \tag{2}$$

And, through rotation, location $\vec{x}_1$ (the location before rotation) can be obtained, for example as described by the following:

$$\vec{x}_1 = \vec{x}_1' \otimes \beta, \tag{3}$$

where $\otimes$ is the rotation operation.

Thus, in some embodiments, motion vector M can be described by the following:

$$\vec{M} = \vec{x}_1 - \vec{x}_0 = (\vec{x}_0 + \vec{M}') \otimes \beta - \vec{x}_0. \tag{4}$$

And a warping field may include a respective motion vector $\vec{M}$ for each pixel, each voxel, each group of pixels, or each group of voxels.

Figure 16:
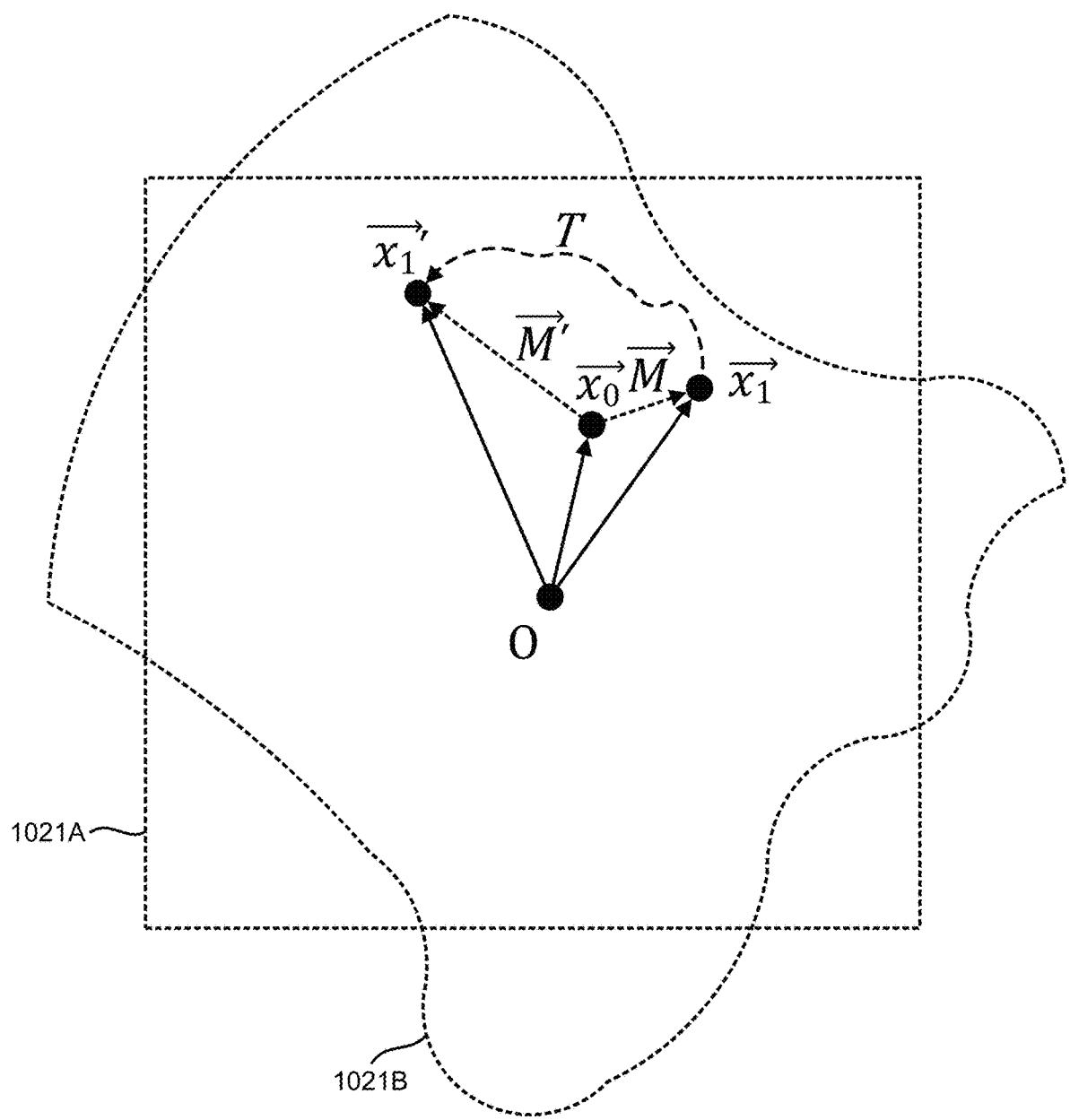
FIG. 16 illustrates another example of a transformation of the point in FIG. 14.

FIG. 16 illustrates another example of a transformation of the point in FIG. 14. In FIG. 16, the invertible transformation T is not limited to a rotation (thus, FIG. 16 is a more general example than FIG. 15). The PAR 1021B that includes the point at location $\vec{x}_1$ was transformed. The transformation T may be based, at least in part, on the detection angle of the PAR 1021B and on the respective detection angles of one or more other PARs (e.g., the detection angle of the PAR that includes the point at location $\vec{x}_0$), or one or more streak angles in the PARs. The transformation T moves the point from location $\vec{x}_1$ to $\vec{x}_1'$. Location $\vec{x}_1'$ may be described by the following:

$$\vec{x}_1' = T(\vec{x}_1). \quad (5)$$

Thus, in some embodiments, motion vector $\vec{M}$ can be described by the following:

$$\vec{M} = \vec{x}_1 - \vec{x}_0 = T^{-1}(\vec{x}_0 + \vec{M}') - \vec{x}_0, \quad (6)$$

where $T^{-1}$ is the inverse of the transform T.

In FIG. 12, after block B1220, the flow moves to block B1225, where the image-generation device generates a motion-corrected reconstruction based on the scan data and on the correspondence-mapping data, which include the motion map that was generated in block B1223 by using the inverse of the transform that was used in block B1221 (the "transformed motion map") in this embodiment. For example, some embodiments of the image-generation device select a reference PAR (e.g., a first capture PAR), move each pixel in each of the other PARs to its location in the reference PAR based on the pixel's respective motion vectors in the motion map, and generate a motion-corrected reconstruction by summing the modified (e.g., warped) PARs and the reference PAR. For example, in FIG. 7C, if PAR 1021A is the reference PAR, then the image-generation device may use each pixel's respective motion vectors in the motion map to move each pixel in the other PARs 1021B-F to their locations in PAR 1021A, thereby generating warped PARs. Then the image-generation device may sum the warped PARs and PAR 1021A, thereby generating a motion-corrected reconstruction.

Finally, the flow ends in block B1230.

Figure 17:
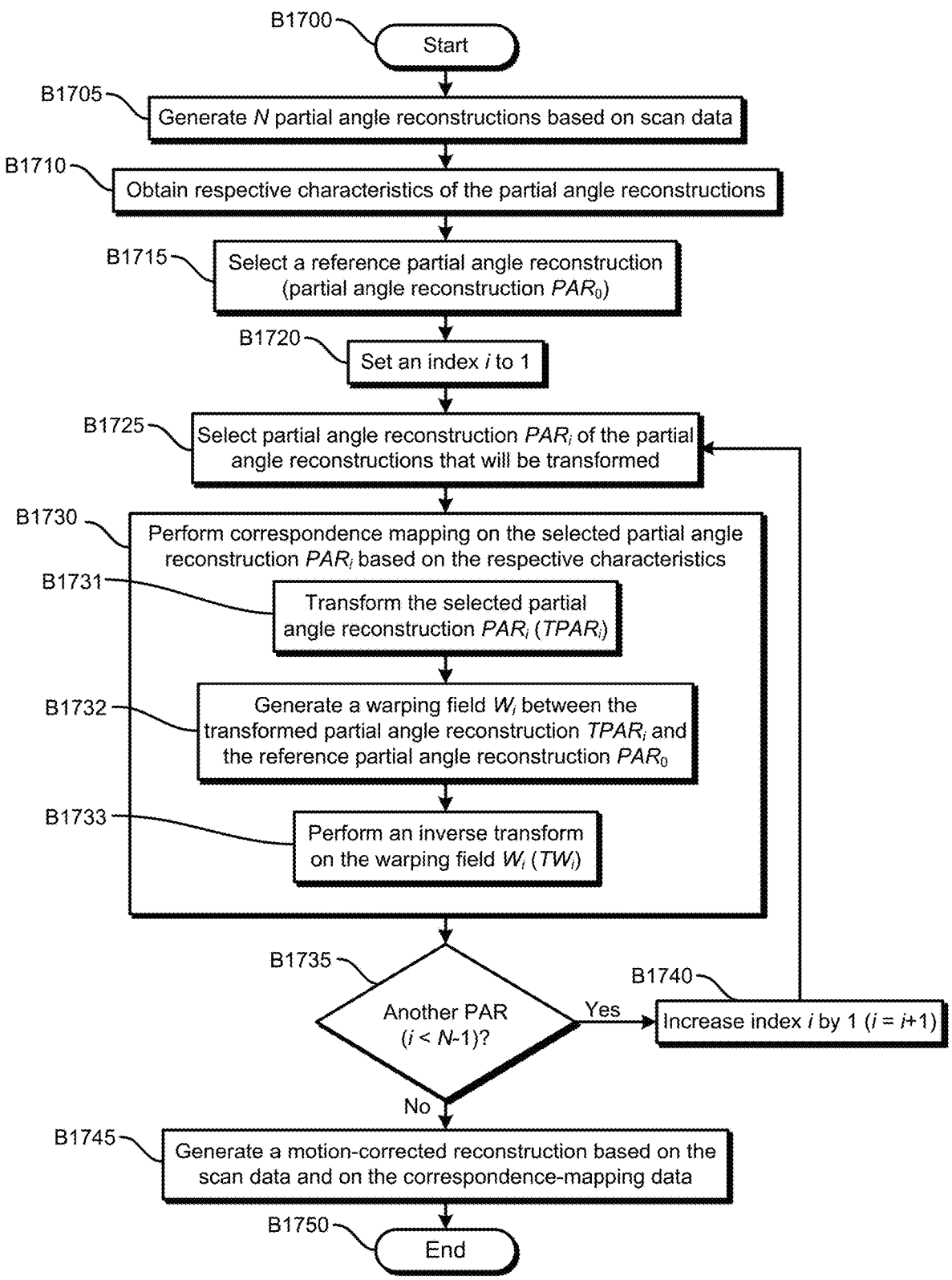
FIG. 17 illustrates an example embodiment of an operational flow for generating a motion-corrected reconstruction.

FIG. 17 illustrates an example embodiment of an operational flow for generating a motion-corrected reconstruction. The flow begins in block B1700 and moves to block B1705, where an image-generation device generates N PARs based on the scan data. Then, in block B1710, the image-generation device obtains respective characteristics of the PARs.

Next, in block B1715, the image-generation device selects a reference PAR $PAR_0$ from among the PARs. In this embodiment, the reference PAR $PAR_0$ is a PAR that will not be transformed.

The flow then proceeds to block B1720, where the image-generation device sets an index i to 1. Then, in block B1725, the image-generation device selects PAR $PAR_i$ of the N−1 PARs that will be transformed (which are the PARs that are not selected as the reference PAR $PAR_0$). Next, in block B1730, the image-generation device performs correspondence mapping on the selected PAR $PAR_i$ based on the respective characteristics. Block B1730 includes blocks B1731-B1733.

In block B1731, the image-generation device transforms the selected PAR $PAR_i$ according to transform T, thereby generating a transformed PAR $TPAR_i$. For example, the image-generation device may transform (e.g., rotate) the selected PAR $PAR_i$ to align (or more closely align) a streak direction in the selected PAR $PAR_i$ with a streak direction of the reference PAR $PAR_0$. In block B1732, the image-generation device generates a motion map, which is a warping field $W_i$ in this embodiment, between the transformed PAR $TPAR_i$ and the reference PAR $PAR_0$. And, in block B1733, the image-generation device performs an inverse of the transform T that was performed in block B1731 on the warping field $W_i$, thereby generating a transformed warping field $TW_i$.

From block B1730, the flow moves to block B1735, where the image-generation device determines whether there is a PAR for which correspondence mapping has not been performed (e.g., whether i<N−1). If the image-generation generation device determines that there is a PAR for which correspondence mapping has not been performed (B1735=Yes), then the flow advances to block B1740, where the image-generation device increases the index i by one, and then the flow returns to block B1725. If the image-generation generation device determines that there is not a PAR for which correspondence mapping has not been performed (B1735=No), then the flow proceeds to block B1745.

In block B1745, the image-generation device generates a motion-corrected reconstruction based on the scan data and on the transformed warping fields ($TW_1, TW_2, \ldots TW_{N-1}$). Finally, the flow ends in block B1750.

Figure 18:
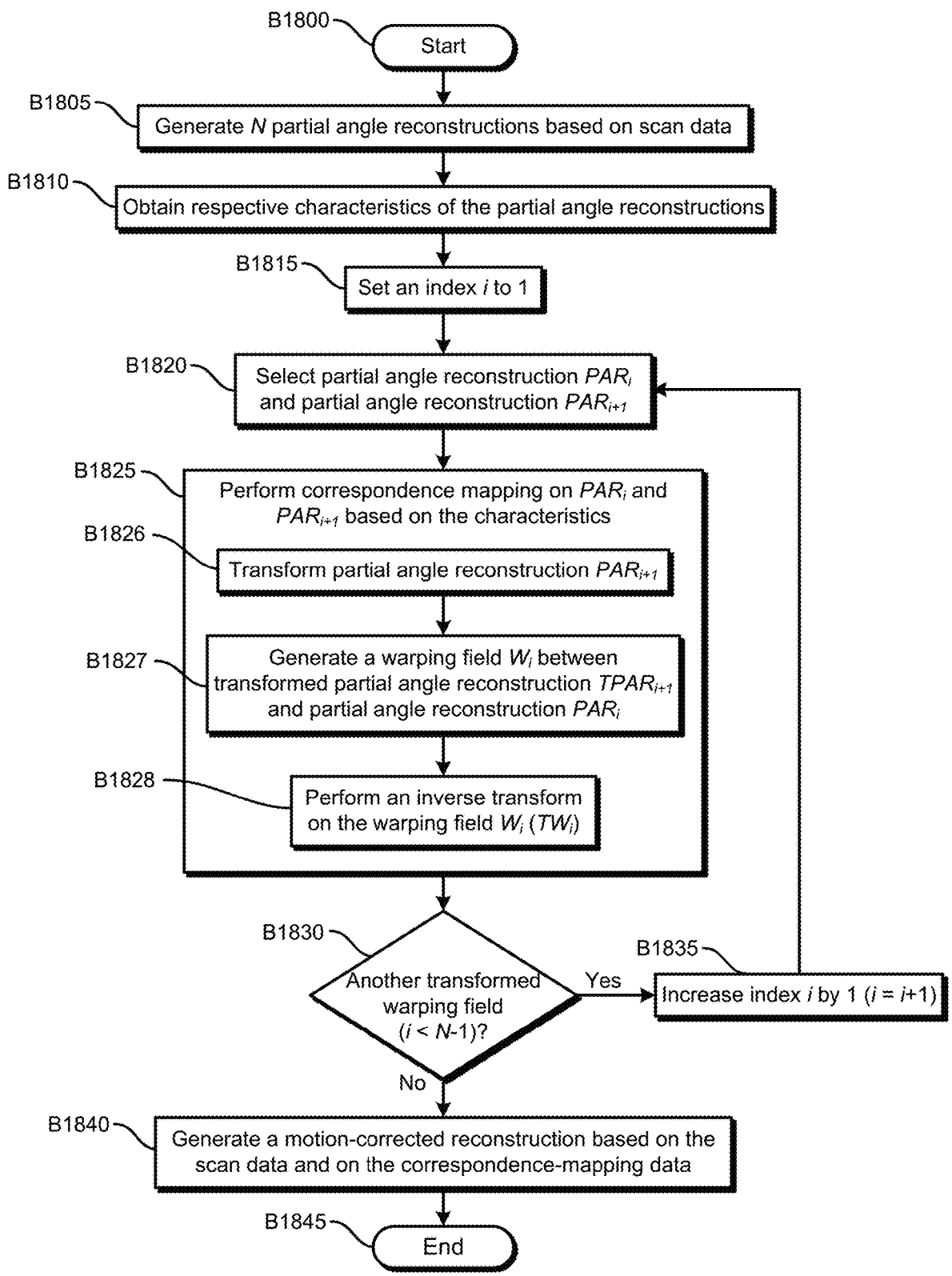
FIG. 18 illustrates an example embodiment of an operational flow for generating a motion-corrected reconstruction.

FIG. 18 illustrates an example embodiment of an operational flow for generating a motion-corrected reconstruction. The flow begins in block B1800 and moves to block B1805, where an image-generation device generates N PARs based on the scan data. The flow then advances to block B1810, where the image-generation device obtains respective characteristics of the PARs.

Next, in block B1815, the image-generation device sets an index i to 1. Also, the PARs may be sorted by angle of detection. For example, the PARs may be sorted such that the detection angle of PAR $PAR_1$ is closest to the detection angel of PAR $PAR_2$ (i.e., no PAR has a detection angle that is between the detection angle of PAR $PAR_1$ and the detection angel of PAR $PAR_2$).

Then, in block B1820, the image-generation device selects PAR $PAR_i$ and selects PAR $PAR_{i+1}$ of the N PARs. Next, in block B1825, the image-generation device performs correspondence mapping on PAR $PAR_i$ and on PAR $PAR_{i+1}$ based, at least in part, on the characteristics. Block B1825 includes blocks B1826-B1828.

In block B1826, the image-generation device transforms PAR $PAR_{i+1}$, thereby generating transformed PAR $TPAR_{i+1}$. For example, the image-generation device may transform (e.g., rotate) PAR $PAR_{i+1}$ to align (or more closely align) a streak direction in PAR $PAR_{i+1}$ with a streak direction in PAR $PAR_i$. In block B1827, the image-generation device generates a motion map, which is a warping field $W_i$ in this embodiment, between transformed PAR $TPAR_{i+1}$ and PAR $PAR_i$. And, in block B1828, the image-generation device performs an inverse transform (an inverse of the transform from block B1826) on the warping field $W_i$, thereby generating correspondence-mapping data that include a transformed motion map (transformed warping field $TW_i$).

From block B1825, the flow moves to block B1830, where the image-generation device determines whether to generate another transformed warping field (e.g., whether i<N−1). For example, in embodiments in which the PARs are sorted by detection angle, the image-generation device may determine whether a transformed warping field has been generated for each pair of adjacent PARs. If the image-generation generation device determines to generate another transformed warping field (B1830=Yes), then the flow advances to block B1835, where the image-generation device increases the index i by one, and then the flow returns to block B1820. If the image-generation generation device determines not to generate another transformed warping field (B1830=No), then the flow proceeds to block B1840.

In block B1840, the image-generation device generates a motion-corrected reconstruction based on the PARs (or on the scan data) and on the correspondence-mapping data, which include the transformed warping fields (TW$_1$, TW$_2$, ... TW$_{N-1}$). Some embodiments of the image-generation device use multiple transformed warping fields to move a pixel or voxel in a PAR to another location. For example, to move a pixel in PAR PAR$_3$ to that pixel's location in PAR PAR$_1$, the image-generation device may use transformed warping fields TW$_1$ and TW$_2$ (e.g., by using the sum of the respective motion vectors of the pixel in the transformed warping fields TW$_1$ and TW$_2$).

Finally, the flow ends in block B1845.

Figure 19:
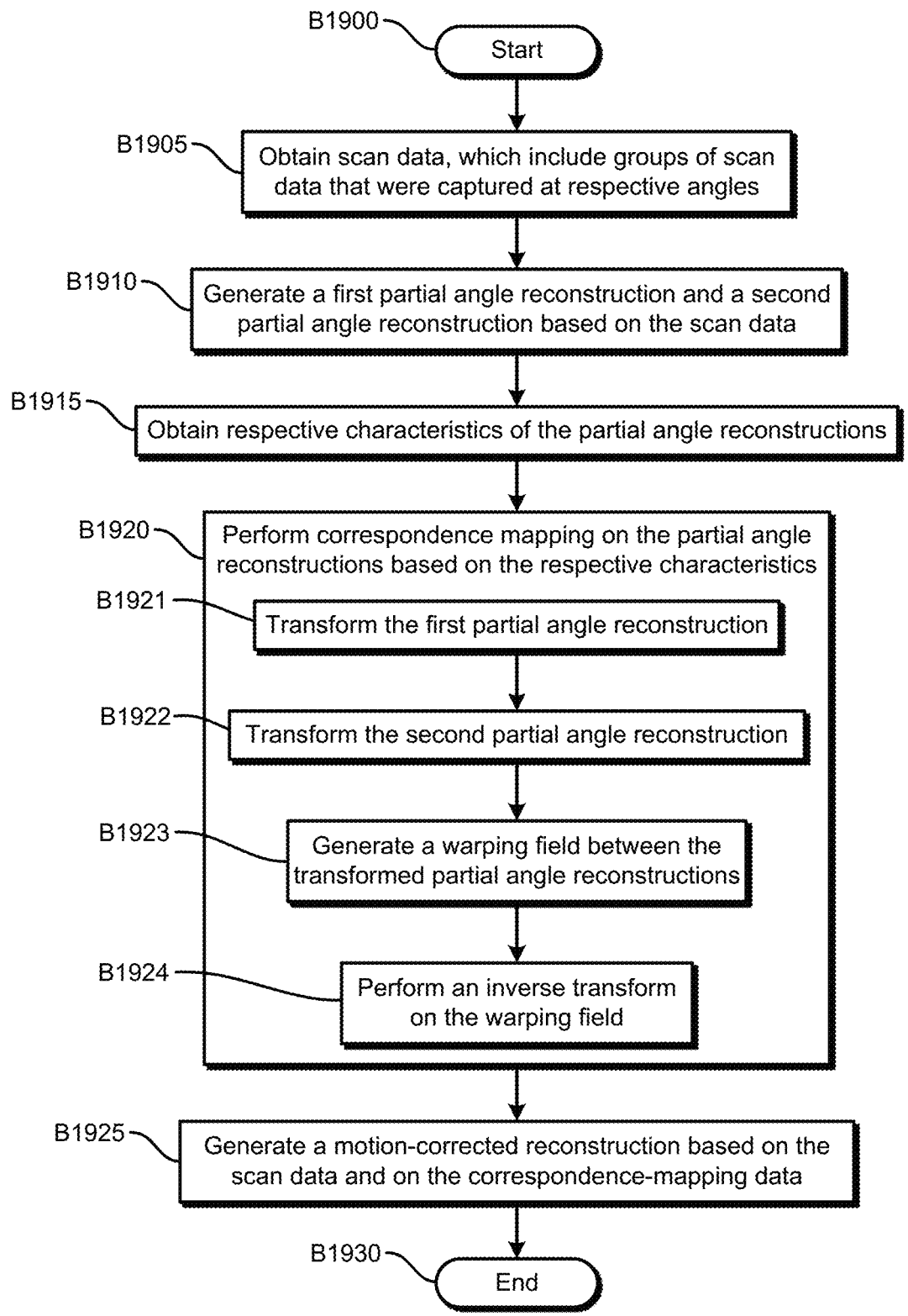
FIG. 19 illustrates an example embodiment of an operational flow for generating a motion-corrected reconstruction.

FIG. 19 illustrates an example embodiment of an operational flow for generating a motion-corrected reconstruction. The flow begins in block B1900 and moves to block B1905, where an image-generation device obtains scan data, which include groups of scan data that were captured at respective detection angles. Next, in block B1910, the image-generation device generates a first PAR and a second PAR based on the scan data. And, in block B1915, the image-generation device obtains respective characteristics of the PARs.

The flow then proceeds to block B1920, where the image-generation device performs correspondence mapping on the PARs. Block B1920 includes blocks B1921-B1924.

In block B1921, the image-generation device transforms the first PAR. Then, in block B1922, the image-generation device transforms the second PAR.

Next, in block B1923, the image-generation device generates a motion map, which is a warping field in this embodiment, between the transformed first and second PARs. The flow then moves to block B1924, where the image-generation device performs an inverse transform (an inverse of the transform that was performed in block B1921 or in block B1922) on the warping field.

Figure 20:
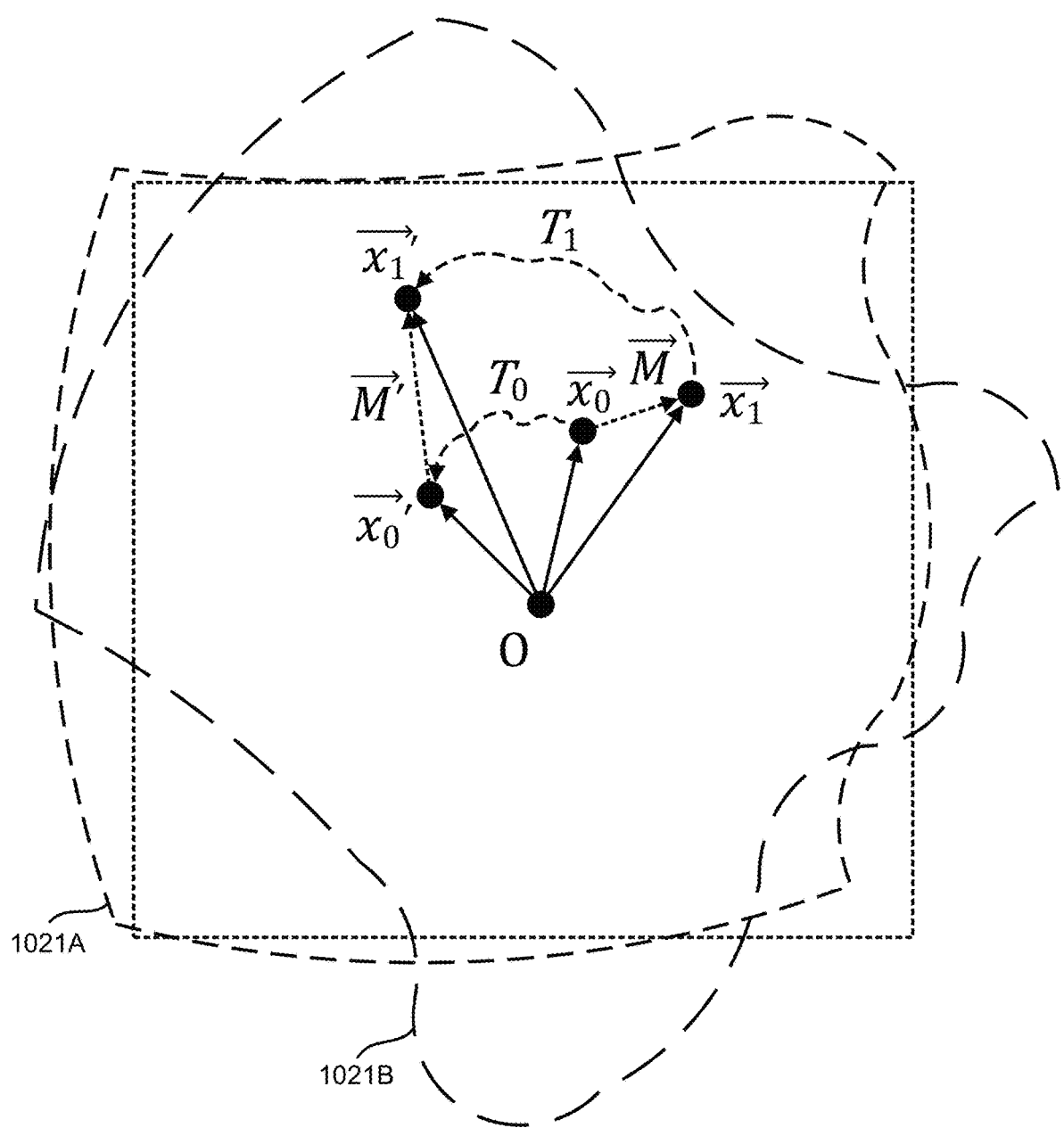
FIG. 20 illustrates an example of two transformations of the point in FIG. 14.

For example, FIG. 20 illustrates an example of two transformations of the point in FIG. 14. The first PAR 1021A, which includes the point at location $\vec{x}_0$, was transformed according to a first transformation $T_0$, and the second PAR 1021B, which includes the point at location $\vec{x}_1$, was transformed according to a second transformation $T_1$. The first transformation $T_0$ may be identical to the second transformation $T_1$, or they may be different. Thus, in the first PAR 1021A, the point moves from location $\vec{x}_0$ to $\vec{x}_0'$, and, in the second PAR 1021B, the point moves from location $\vec{x}_1$ to $\vec{x}_1'$. Location $\vec{x}_0'$ may be described by the following:

$$\vec{x}_0' = T_0(\vec{x}_0). \qquad (7)$$

And location $\vec{x}_1'$ may be described by the following:

$$\vec{x}_1' = T_1(\vec{x}_1). \qquad (8)$$

Because $$\vec{x}_1' = \vec{x}_0' + \vec{M}, \qquad (9)$$

motion vector $\vec{M}$ can be described by the following:

$$\vec{M} = \vec{x}_1 - \vec{x}_0 = T_1^{-1}(T_0(\vec{x}_0) + \vec{M}) - \vec{x}_0, \qquad (10)$$

where $T_1^{-1}$ is the inverse of the transform $T_1$.

In FIG. 19, after block B1920, the flow moves to block B1925, where the image-generation device generates a motion-corrected reconstruction based on the scan data and on the correspondence-mapping data, which include the transformed warping field. Finally, the flow ends in block B1930.

Figure 21:
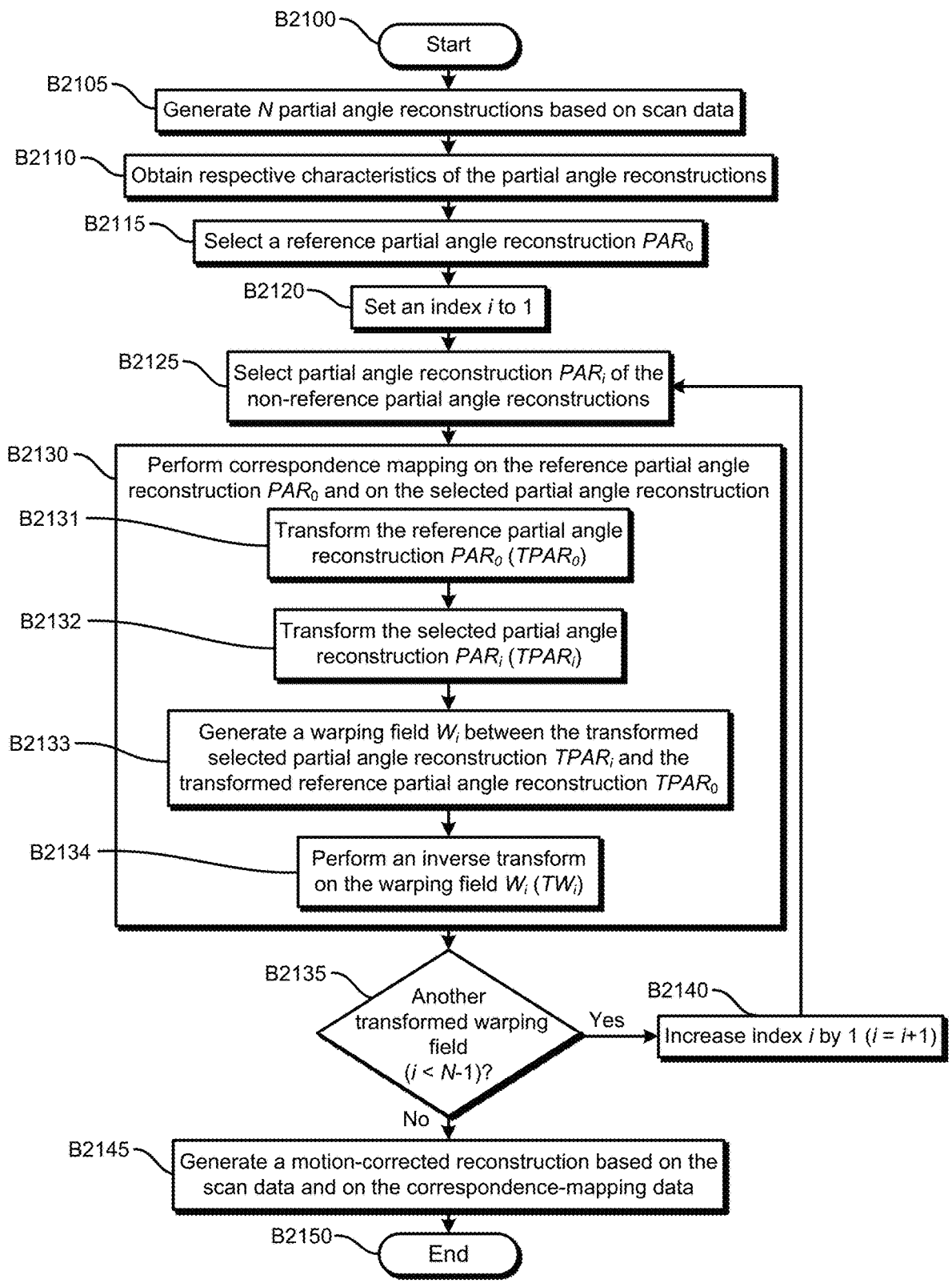
FIG. 21 illustrates an example embodiment of an operational flow for generating a motion-corrected reconstruction.

FIG. 21 illustrates an example embodiment of an operational flow for generating a motion-corrected reconstruction. The flow begins in block B2100 and moves to block B2105, where an image-generation device generates N PARs based on the scan data. Next, in block B2110, the image-generation device obtains respective characteristics of the PARs.

Then, in block B2115, the image-generation device selects a reference PAR PAR$_0$. And, in block B2120, the image-generation device sets an index i to 1. The flow then moves to block B2125, where the image-generation device selects PAR PAR$_i$ of the N−1 non-reference PARs. Next, in block B2130, the image-generation device performs correspondence mapping on the reference PAR PAR$_0$ and on the selected PAR PAR$_i$ based, at least in part, on the respective characteristics. Block B2130 includes blocks B2131-B2134.

In block B2131, the image-generation device transforms the reference PAR PAR$_0$, thereby generating a transformed reference PAR TPAR$_0$. And, in block B2132, the image-generation device transforms the selected PAR PAR$_i$, thereby generating a transformed selected PAR TPAR$_i$. The transforms used in blocks B2131 and B2132 may be identical, or they may be different. Also, the transform used in block B2131 may be the same in every iteration, or the transform may be different in at least some iterations of block B2131. Similarly, the transform used in block B2132 may be the same in every iteration, or the transform may be different in at least some iterations of block B2132.

Next, in block B2133, the image-generation device generates a motion map, which is a warping field W$_i$ in this embodiment, between the transformed reference PAR TPAR$_0$ and the transformed selected PAR TPAR$_i$. And, in block B2134, the image-generation device performs an inverse transform on the warping field W$_i$, thereby generating correspondence-mapping data, which include a transformed warping field TW$_i$ in this embodiment. In this embodiment, the inverse transform is an inverse of the transform that was performed in block B2132, although in some embodiments the inverse transform is an inverse of the transform that was performed in block B2131.

From block B2130, the flow moves to block B2135, where the image-generation device determines whether to generate another transformed warping field (e.g., whether i<N−1). If the image-generation generation device determines to generate another transformed warping field (B2135=Yes), then the flow advances to block B2140, where the image-generation device increases the index i by one, and then the flow returns to block B2125. If the image-generation generation device determines not to generate another transformed warping field (B2135=No), then the flow proceeds to block B2145.

In block B2145, the image-generation device generates a motion-corrected reconstruction based on the scan data and on the transformed warping fields (TW$_1$, TW$_2$, ... TW$_{N-1}$). Finally, the flow ends in block B2150.

Figure 22:
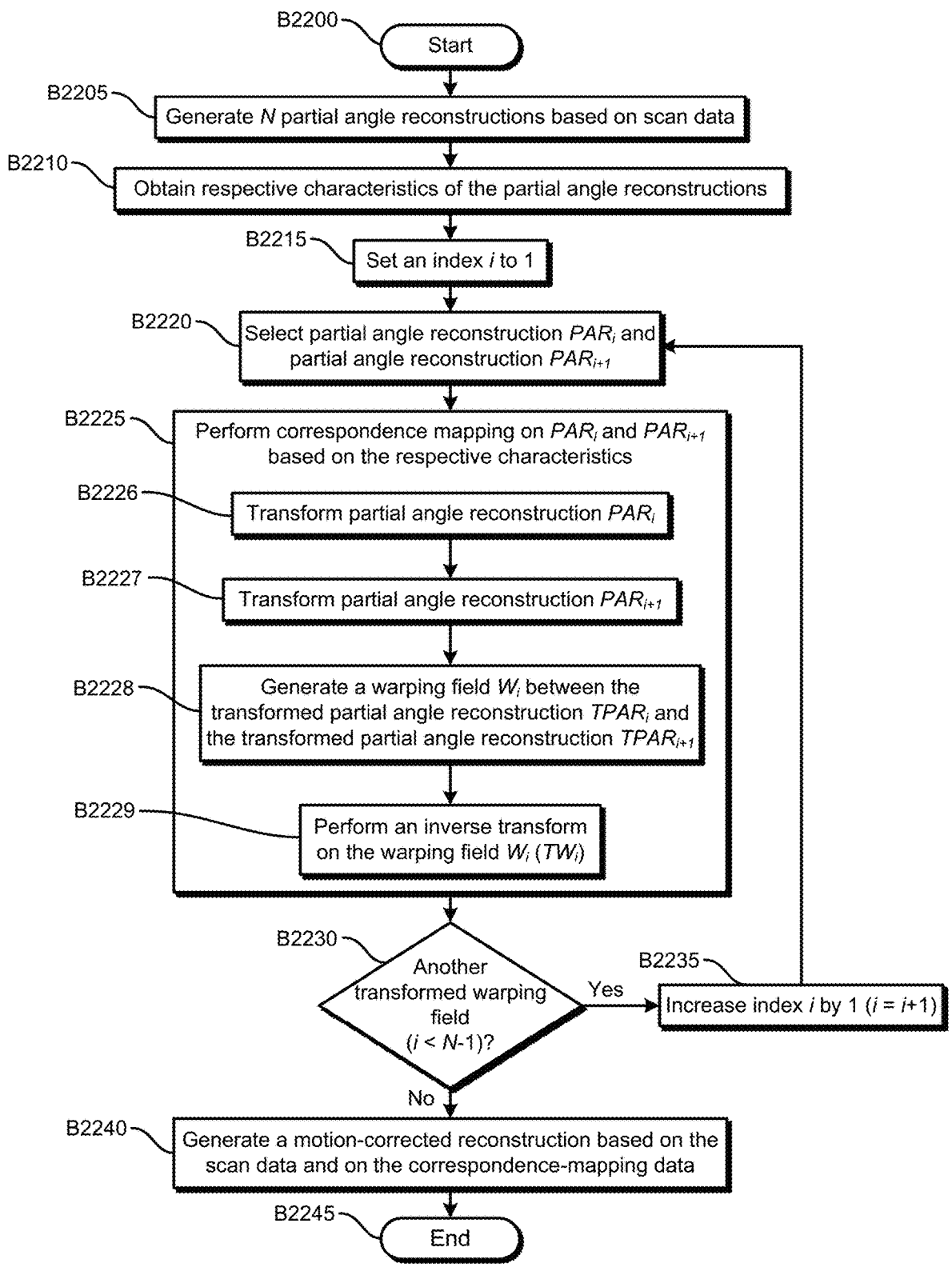
FIG. 22 illustrates an example embodiment of an operational flow for generating a motion-corrected reconstruction.

FIG. 22 illustrates an example embodiment of an operational flow for generating a motion-corrected reconstruction. The flow begins in block B2200 and moves to block B2205, where an image-generation device generates N PARs based on the scan data. And, in block B2210, the image-generation device obtains respective characteristics of the PARs.

Next, in block B2215, the image-generation device sets an index i to 1. Also, the PARs may be sorted by angle of detection. Then, in block B2220, the image-generation device selects PAR $PAR_i$ and selects PAR $PAR_{i+1}$ of the N PARs. Next, in block B2225, the image-generation device performs correspondence mapping on PAR $PAR_i$ and on PAR $PAR_{i+1}$ based, at least in part, on the respective characteristics. Block B2225 includes blocks B2226-B2229.

In block B2226, the image-generation device transforms the first selected PAR $PAR_i$, thereby generating a first transformed PAR $TPAR_i$. In block B2227, the image-generation device transforms the second selected PAR $PAR_{i+1}$, thereby generating a second transformed PAR $TPAR_{i+1}$. The transforms used in blocks B2226 and B2227 may be identical, or they may be different. Also, the transform used in block B2226 may be the same in every iteration, or the transform may be different in at least some iterations of block B2226. Similarly, the transform used in block B2227 may be the same in every iteration, or the transform may be different in at least some iterations of block B2227.

In block B2228, the image-generation device generates a motion map, which is a warping field $W_i$ in this embodiment, between the first transformed PAR $TPAR_i$ and the second transformed PAR $TPAR_{i+1}$. And, in block B2229, the image-generation device performs an inverse transform on the warping field $W_i$, thereby generating a transformed warping field $TW_i$. The inverse transform may be an inverse of the transform from block B2226, or the inverse transform may be an inverse of the transform from block B2227.

From block B2225, the flow moves to block B2230, where the image-generation device determines whether to generate another transformed warping field (e.g., whether i<N−1). For example, in embodiments in which the PARs are sorted by detection angle, the image-generation device may determine whether a transformed warping field has been generated for each pair of adjacent PARs. If the image-generation generation device determines to generate another transformed warping field (B2230=Yes), then the flow advances to block B2235, where the image-generation device increases the index i by one, and then the flow returns to block B2220. If the image-generation generation device determines not to generate another transformed warping field (B2230=No), then the flow proceeds to block B2240.

In block B2240, the image-generation device generates a motion-corrected reconstruction based on the scan data and on the correspondence-mapping data, which include the transformed warping fields ($TW_1$, $TW_2$, $TW_{N-1}$). Finally, the flow ends in block B2245.

The operational flows in FIGS. 12, 17-19, and 21-22 may allow image registration to be performed in cases where image registration could not otherwise be performed. Also, the operational flows in FIGS. 12, 17-19, and 21-22 may provide more accurate image registration in cases where direct image registration would be degraded by artifacts and other image defects.

Figure 23:
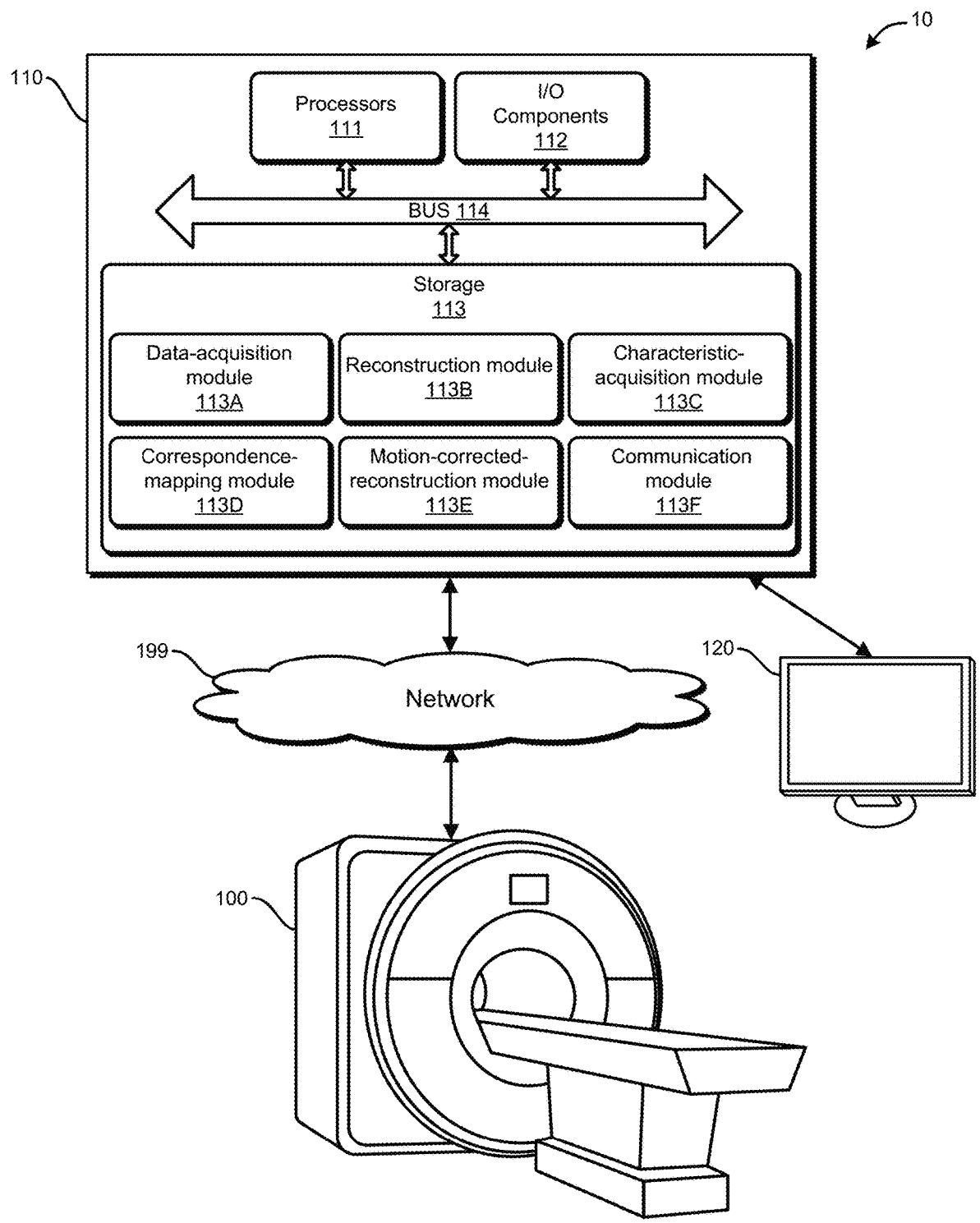
FIG. 23 illustrates an example embodiment of a medical-imaging system.

FIG. 23 illustrates an example embodiment of a medical-imaging system. The system 10 includes a scanning device 100; an image-generation device 110, which is a specially-configured computing device; and a display device 120. In this embodiment, the image-generation device 110 and the scanning device 100 communicate via one or more networks 199, which may include a wired network, a wireless network, a LAN, a WAN, a MAN, and a PAN. Also, in some embodiments the devices communicate via other wired or wireless channels.

The image-generation device 110 includes one or more processors 111, one or more I/O components 112, and storage 113. And the hardware components of the image-generation device 110 communicate via one or more buses 114 or other electrical connections. Examples of buses 114 include a universal serial bus (USB), an IEEE 1394 bus, a PCI bus, an Accelerated Graphics Port (AGP) bus, a Serial AT Attachment (SATA) bus, and a Small Computer System Interface (SCSI) bus.

The one or more processors 111 include one or more central processing units (CPUs), which include microprocessors (e.g., a single core microprocessor, a multi-core microprocessor); one or more graphics processing units (GPUs); one or more application-specific integrated circuits (ASICs); one or more field-programmable-gate arrays (FPGAs); one or more digital signal processors (DSPs); or other electronic circuitry (e.g., other integrated circuits). The I/O components 112 include communication components (e.g., a GPU, a network-interface controller) that communicate with the display device 120, the network 199, the scanning device 100, and input or output devices (not illustrated), which may include a keyboard, a mouse, a printing device, a touch screen, a light pen, an optical-storage device, a scanner, a microphone, a drive, a joystick, and a control pad.

The storage 113 includes one or more computer-readable storage media. As used herein, a computer-readable storage medium refers to a computer-readable medium that includes an article of manufacture, for example a magnetic disk (e.g., a floppy disk, a hard disk), an optical disc (e.g., a CD, a DVD, a Blu-ray), a magneto-optical disk, magnetic tape, and semiconductor memory (e.g., a non-volatile memory card, flash memory, a solid-state drive, SRAM, DRAM, EPROM, EEPROM). The storage 113, which may include both ROM and RAM, can store computer-readable data or computer-executable instructions.

The image-generation device 110 additionally includes a data-acquisition module 113A, a reconstruction module 113B, a characteristic-acquisition module 113C, a correspondence-mapping module 113D, a motion-corrected-reconstruction module 113E, and a communication module 113F. A module includes logic, computer-readable data, or computer-executable instructions. In the embodiment shown in FIG. 23, the modules are implemented in software (e.g., Assembly, C, C++, C#, Java, BASIC, Perl, Visual Basic). However, in some embodiments, the modules are implemented in hardware (e.g., customized circuitry) or, alternatively, a combination of software and hardware. When the modules are implemented, at least in part, in software, then the software can be stored in the storage 113. Also, in some embodiments, the image-generation device 110 includes additional or fewer modules, the modules are combined into fewer modules, or the modules are divided into more modules.

The data-acquisition module 113A includes instructions that cause the image-generation device 110 to obtain scan data from the scanning device 100. For example, some embodiments of the data-acquisition module 113A include instructions that cause the image-generation device 110 to perform at least some of the operations that are described in block B310 in FIG. 3, in block B605 in FIG. 6, in block B805 in FIG. 8, in block B1105 in FIG. 11, in block B1205 in FIG. 12, in block B1805 in FIG. 18, in block B1905 in FIG. 19, in block B2105 in FIG. 21, and in block B2205 in FIG. 22.

The reconstruction module 113B includes instructions that cause the image-generation device 110 to generate full reconstructions, half reconstructions, and PARs, which may include patch PARs and contour PARs. For example, some embodiments of the reconstruction module 113B include instructions that cause the image-generation device 110 to perform at least some of the operations that are described in block B320 in FIG. 3; in blocks B610 and B620 in FIG. 6; in blocks B810, B820, and B840 in FIG. 8; in blocks B1110 and B1120 in FIG. 11; in block B1210 in FIG. 12; in block B1705 in FIG. 17; in block B1805 in FIG. 18; in block B1910 in FIG. 19; in block B2105 in FIG. 21; and in block B2205 in FIG. 22.

The characteristic-acquisition module 113C includes instructions that cause the image-generation device 110 to obtain respective characteristics of one or more reconstructions (e.g., PARs, half reconstructions, full reconstructions). For example, some embodiments of the characteristic-acquisition module 113C include instructions that cause the image-generation device 110 to perform at least some of the operations that are described in block B210 in FIG. 2, in block B330 in FIG. 3, in block B625 in FIG. 6, in block B825 in FIG. 8, in block B1125 in FIG. 11, in block B1215 in FIG. 12, in block B1710 in FIG. 17, in block B1810 in FIG. 18, in block B1915 in FIG. 19, in block B2110 in FIG. 21, and in block B2210 in FIG. 22.

The correspondence-mapping module 113D includes instructions that cause the image-generation device 110 to perform correspondence mapping on two or more PARs based, at least in part, on characteristics of the PARs. The correspondence mapping may include performing one or more transforms or image registration, and the correspondence mapping generates correspondence-mapping data, which may include one or more motion maps (e.g., warping fields) and transforms. For example, some embodiments of the correspondence-mapping module 113D include instructions that cause the image-generation device 110 to perform at least some of the operations that are described in block B220 in FIG. 2, in block B340 in FIG. 3, in block B630 in FIG. 6, in block B830 in FIG. 8, in block B1130 in FIG. 11, in block B1220 in FIG. 12, in blocks B1720-B1740 in FIG. 17, in blocks B1815-B1835 in FIG. 18, in block B1920 in FIG. 19, in blocks B2120-B2140 in FIG. 21, and in blocks B2215-B2235 in FIG. 22.

The motion-corrected-reconstruction module 113E includes instructions that cause the image-generation device 110 to generate motion-corrected reconstructions of based on correspondence-mapping data and based on PARs or on scan data. For example, some embodiments of the motion-corrected-reconstruction module 113E include instructions that cause the image-generation device 110 to perform at least some of the operations that are described in block B230 in FIG. 2, in block B350 in FIG. 3, in blocks B635 and B645 in FIG. 6, in blocks B835 and B845 in FIG. 8, in blocks B1135 and B1140 in FIG. 11, in block B1225 in FIG. 12, in block B1745 in FIG. 17, in block B1840 in FIG. 18, in block B1925 in FIG. 19, in block B2145 in FIG. 21, and in block B2240 in FIG. 22.

The communication module 113F includes instructions that cause the image-generation device 110 to communicate with other devices, such as the display device 120, the scanning device 100, and other computing devices. For example, the communication module 113F includes instructions that cause the image-generation device 110 to display reconstructions (e.g., motion-corrected reconstructions) on the display device 120.

The scope of the claims is not limited to the above-described embodiments and includes various modifications and equivalent arrangements.

The invention claimed is:

1. A medical image processing apparatus for correcting motion artifacts in a medical image, the medical image processing apparatus comprising:
   receiving circuitry configured to receive scan data that were generated by scanning a region of a subject with a computed tomography apparatus; and
   processing circuitry configured to perform:
      generating multiple partial angle reconstruction (PAR) images based on the scan data,
      obtaining corresponding characteristics of the multiple PAR images,
      correspondence mapping on the multiple PAR images based on the obtained corresponding characteristics and on the multiple PAR images, wherein the correspondence mapping generates correspondence-mapping data, and wherein the correspondence mapping includes performing image registration on at least some of the multiple PAR images, and
      generating a motion-corrected reconstruction image based on the correspondence-mapping data and on one or both of the scan data and the PAR images.

2. The medical image processing apparatus of claim 1, wherein the scan data include sets of projections of predetermined ranges of a scan angle.

3. The medical image processing apparatus of claim 2, wherein at least some of the predetermined ranges of the scan angle at least partially overlap.

4. The medical image processing apparatus of claim 2, wherein generating the motion-corrected reconstruction image includes performing a summation process of the registered multiple PAR images.

5. The medical image processing apparatus of claim 1, wherein the multiple PAR images are three-dimensional images, and
   wherein generating the motion-corrected reconstruction image is based on the three-dimensional images.

6. The medical image processing apparatus of claim 1, wherein generating multiple PAR images includes:
   a process of reconstructing a reconstruction image based on the scan data;
   a process of segmenting a region of interest in the reconstruction image; and
   a process of identifying the scan data that correspond to the region of interest,
   wherein the multiple PAR images are PARs of the region of interest and are generated based on the identified scan data that correspond to the region of interest.

7. The medical image processing apparatus of claim 6, wherein generating the motion-corrected reconstruction image includes:
   a process of generating a motion-corrected reconstruction image that corresponds to the region of interest; and
   a process of combining the motion-corrected reconstruction image that corresponds to the region of interest and the reconstruction image.

8. The medical image processing apparatus of claim 6, wherein the region of interest includes a vessel.

9. The medical image processing apparatus of claim 1, wherein the correspondence mapping includes performing a transform on one or more of the PAR images.

10. The medical image processing apparatus of claim 9, wherein obtaining the corresponding characteristics of the multiple PAR images includes obtaining a direction of streak artifacts in the multiple PAR images, and
    wherein the transform aligns the directions of the streak artifacts in the multiple PAR images.

11. The medical image processing apparatus of claim 10, wherein the transform includes a rotation.

12. The medical image processing apparatus of claim 9, wherein the correspondence-mapping data include a motion map.

13. The medical image processing apparatus of claim 12, wherein generating the motion-corrected reconstruction image is based on the motion map.

14. The medical image processing apparatus of claim 12, wherein generating the motion map includes performing an inverse of the transform.

15. A medical image processing apparatus comprising:
receiving circuitry configured to receive scan data, wherein the scan data include multiple sets of scan data; and
processing circuitry configured to perform:
generating partial angle reconstruction (PAR) images based on the scan data,
transforming at least one of the PAR images based on characteristics of the multiple sets of scan data to obtain one or more transformed PARs,
generating a motion map based on image registration that is performed at least on the one or more transformed PARs, and
performing an inverse transform on the motion map, thereby generating a transformed motion map.

16. The medical image processing apparatus of claim 15, wherein the processing circuitry is further configured to perform:
generating at least one medical image based on the transformed motion map.

17. A medical image processing system comprising:
one or more medical image processing apparatuses for correcting motion artifacts in a medical image, wherein each of the one or more medical image processing apparatuses includes one or more respective computer-readable media and one or more respective processors, and
wherein the one or more respective computer-readable media and one or more respective processors of the one or more medical image processing apparatuses cooperate to perform operations that include:
receiving scan data that were generated by scanning a region of a subject with a computed tomography apparatus;
generating multiple partial angle reconstruction (PAR) images based on the scan data;
obtaining corresponding characteristics of the multiple PAR images;
performing correspondence mapping on the multiple PAR images based on the obtained corresponding characteristics and on the multiple PAR images, wherein the correspondence mapping generates correspondence-mapping data, and wherein performing the correspondence mapping includes performing image registration on at least some of the multiple PAR images; and
generating a motion-corrected reconstruction image based on the correspondence-mapping data and on one or both of the scan data and the PAR images.

18. A method comprising:
receiving scan data that were generated by scanning a region of a subject with a computed tomography apparatus;
generating multiple partial angle reconstruction (PAR) images based on the scan data;
obtaining corresponding characteristics of the multiple PAR images;
performing correspondence mapping on the multiple PAR images based on the obtained corresponding characteristics and on the multiple PAR images, wherein the correspondence mapping generates correspondence-mapping data, and wherein performing the correspondence mapping includes performing image registration on at least some of the multiple PAR images; and
generating a motion-corrected reconstruction image based on the correspondence-mapping data and on one or both of the scan data and the PAR images.

19. One or more computer-readable storage media storing instructions that, when executed by one or more computing devices, cause the one or more computing devices to perform operations comprising:
receiving scan data that were generated by scanning a region of a subject with a computed tomography apparatus;
generating multiple partial angle reconstruction (PAR) images based on the scan data;
obtaining corresponding characteristics of the multiple PAR images;
performing correspondence mapping on the multiple PAR images based on the obtained corresponding characteristics and on the multiple PAR images, wherein the correspondence mapping generates correspondence-mapping data, and wherein performing the correspondence mapping includes performing image registration on at least some of the multiple PAR images; and
generating a motion-corrected reconstruction image based on the correspondence-mapping data and on one or both of the scan data and the PAR images.

20. A method comprising:
receiving scan data, wherein the scan data include multiple sets of scan data;
generating partial angle reconstruction (PAR) images based on the scan data;
transforming at least one of the PAR images based on characteristics of the multiple sets of scan data to obtain at least one transformed PAR image;
generating a motion map based on image registration that is performed on the at least one transformed PAR image; and
performing an inverse transform on the motion map, thereby generating a transformed motion map.

21. The method of claim 20, wherein the image registration is further performed on at least one of the PAR images.

22. The method of claim 20, wherein the at least one transformed PAR image includes two transformed PAR images, and wherein the image registration is performed on the two transformed PAR images.

* * * * *